US012648860B1

(12) United States Patent (10) Patent No.: US 12,648,860 B1
Garvey et al. (45) Date of Patent: Jun. 9, 2026

(54) INSTRUMENTS AND METHOD FOR ANKLE REPLACEMENT SURGERY

(71) Applicant: RESTOR3D, INC., Durham, NC (US)

(72) Inventors: Brian Garvey, Raleigh, NC (US);
Deepak Padmanabhan, Durham, NC (US)

(73) Assignee: RESTOR3D, INC., Durham, NC (US)

( * ) Notice: Subject to any disclaimer, the term of this patent is extended or adjusted under 35 U.S.C. 154(b) by 0 days.

(21) Appl. No.: 18/511,696

(22) Filed: Nov. 16, 2023

Related U.S. Application Data

(62) Division of application No. 17/025,151, filed on Sep. 18, 2020, now Pat. No. 11,844,704.

(60) Provisional application No. 62/902,181, filed on Sep. 18, 2019.

(51) Int. Cl.
*A61F 2/46* (2006.01)
*A61F 2/30* (2006.01)

(52) U.S. Cl.
CPC .. *A61F 2/4606* (2013.01); *A61F 2002/30433* (2013.01); *A61F 2002/3054* (2013.01); *A61F 2002/4627* (2013.01); *A61F 2002/4687* (2013.01)

(58) Field of Classification Search
CPC ............ A61B 17/1697; A61B 17/8861; A61B 17/8897; A61B 17/846; A61B 17/86; A61B 17/72; A61B 17/7208; A61B 17/725; A61B 17/34; A61B 17/3417; A61M 25/09; A61M 2025/09058; A61M 2025/09175
See application file for complete search history.

(56) References Cited

U.S. PATENT DOCUMENTS

| | | |
|---|---|---|
| 1,428,247 A | 9/1922 | Morris |
| D220,184 S | 3/1971 | Boone |
| 3,872,519 A | 3/1975 | Giannestras |
| | (Continued) | |

FOREIGN PATENT DOCUMENTS

| | | |
|---|---|---|
| CN | 304140566 S | 5/2017 |
| CN | 109567913 A | 4/2019 |
| | (Continued) | |

OTHER PUBLICATIONS

Extended European Search Report dated Feb. 12, 2021 for European Patent Application No. EP20196410.3.
(Continued)

*Primary Examiner* — Anu Ramana
(74) *Attorney, Agent, or Firm* — Husch Blackwell LLP; Bryan D. Stewart; Andrew C. Landsman

(57) ABSTRACT

The present disclosure generally discloses instruments and methods of using those instruments for performing various aspects of ankle replacement surgery. In one embodiment, an alignment assembly for adjusting a position of a guide tool relative to a patient is provided. The alignment assembly includes a proximal housing; a distal housing configured to be connected to the guide tool; and at least one linkage system configured to adjust a relative angle between at least two portions of the alignment assembly. A surgical guide wire is also disclosed. The surgical guide wire includes a distal tip having a tapered or trocar end configured for insertion into a bone; a distal region adjacent to the distal tip; a transition region adjacent to the distal region; and a proximal region adjacent to the transition region.

8 Claims, 16 Drawing Sheets

US 12,648,860 B1

Page 2

(56) References Cited

U.S. PATENT DOCUMENTS

| | | | |
|---|---|---|---|
| D242,957 S | 1/1977 | Treace | |
| 4,207,627 A | 6/1980 | Cloutier | |
| 4,232,404 A | 11/1980 | Samuelson et al. | |
| D265,288 S | 7/1982 | Mclean | |
| 4,440,835 A | 4/1984 | Vignaud | |
| 4,586,933 A | 5/1986 | Shoji et al. | |
| 4,588,574 A | 5/1986 | Felder et al. | |
| 4,829,152 A | 5/1989 | Rostoker | |
| D309,185 S | 7/1990 | Lockawich | |
| 4,944,756 A | 7/1990 | Kenna | |
| 5,137,536 A | 8/1992 | Koshino | |
| D336,517 S | 6/1993 | McKeown | |
| 5,248,456 A | 9/1993 | Evans, Jr. et al. | |
| D358,211 S | 5/1995 | Cohen | |
| D358,647 S | 5/1995 | Cohen et al. | |
| 5,497,783 A * | 3/1996 | Urick | A61M 25/09 600/585 |
| 5,497,785 A * | 3/1996 | Viera | A61M 25/09 600/585 |
| 5,497,786 A * | 3/1996 | Urick | A61M 25/09 600/585 |
| 5,591,191 A * | 1/1997 | Kieturakis | A61B 17/3417 604/164.01 |
| 5,766,259 A | 6/1998 | Sammarco | |
| 5,947,965 A * | 9/1999 | Bryan | A61B 17/7011 606/279 |
| 6,183,519 B1 | 2/2001 | Bonnin | |
| 6,419,491 B1 | 7/2002 | Ricci | |
| 6,461,358 B1 | 10/2002 | Faccioli | |
| D490,901 S | 6/2004 | Schulter et al. | |
| D493,890 S | 8/2004 | Schulter et al. | |
| 6,989,003 B2 * | 1/2006 | Wing | A61B 17/34 604/161 |
| 7,001,672 B2 | 2/2006 | Justin et al. | |
| D521,642 S | 5/2006 | Dorahy | |
| 7,048,741 B2 | 5/2006 | Swanson | |
| 7,125,423 B2 | 10/2006 | Hazebrouck | |
| 7,172,627 B2 | 2/2007 | Fiere et al. | |
| D539,426 S | 3/2007 | Callaghan | |
| 7,468,075 B2 | 12/2008 | Lang et al. | |
| D593,202 S | 5/2009 | Petersen | |
| 7,534,246 B2 | 5/2009 | Reiley | |
| 7,534,263 B2 | 5/2009 | Burdulis, Jr. et al. | |
| 7,534,270 B2 | 5/2009 | Ball | |
| D595,853 S | 7/2009 | Hanson | |
| D598,094 S | 8/2009 | Alber | |
| D604,153 S | 11/2009 | Wantz | |
| 7,618,451 B2 | 11/2009 | Berez et al. | |
| 7,632,575 B2 | 12/2009 | Justin et al. | |
| 7,634,119 B2 | 12/2009 | Tsougarakis et al. | |
| 7,666,522 B2 | 2/2010 | Justin et al. | |
| D611,147 S | 3/2010 | Hanson et al. | |
| 7,717,956 B2 | 5/2010 | Lang | |
| D618,800 S | 6/2010 | Mayon et al. | |
| D619,255 S | 7/2010 | Richter et al. | |
| D620,111 S | 7/2010 | Courtney et al. | |
| D623,749 S | 9/2010 | Horton | |
| 7,796,791 B2 | 9/2010 | Tsougarakis et al. | |
| 7,799,077 B2 | 9/2010 | Lang et al. | |
| D626,234 S | 10/2010 | Otto et al. | |
| 7,819,614 B2 | 10/2010 | Versino et al. | |
| D628,344 S | 11/2010 | Raviv | |
| 7,981,158 B2 | 7/2011 | Fitz et al. | |
| 7,981,159 B2 | 7/2011 | Williams et al. | |
| 8,012,216 B2 | 9/2011 | Metzger | |
| 8,062,302 B2 | 11/2011 | Lang et al. | |
| 8,066,708 B2 | 11/2011 | Lang et al. | |
| 8,077,950 B2 | 12/2011 | Tsougarakis et al. | |
| 8,083,745 B2 | 12/2011 | Lang et al. | |
| 8,094,900 B2 | 1/2012 | Steines et al. | |
| 8,105,330 B2 | 1/2012 | Fitz et al. | |
| D653,756 S | 2/2012 | Courtney et al. | |
| 8,122,582 B2 | 2/2012 | Burdulis, Jr. et al. | |
| 8,128,580 B2 * | 3/2012 | Fujimagari | A61M 25/09033 600/585 |
| 8,142,886 B2 | 3/2012 | Noble et al. | |
| D660,432 S | 5/2012 | Braido | |
| D660,966 S | 5/2012 | Sheild | |
| 8,234,097 B2 | 7/2012 | Steines et al. | |
| D666,298 S | 8/2012 | Sibhatu et al. | |
| 8,262,589 B2 * | 9/2012 | Lupton | A61M 25/09 600/585 |
| 8,292,955 B2 | 10/2012 | Robinson et al. | |
| 8,292,965 B2 | 10/2012 | Walker | |
| 8,337,501 B2 | 12/2012 | Fitz et al. | |
| 8,337,507 B2 | 12/2012 | Lang et al. | |
| D675,320 S | 1/2013 | Oi | |
| 8,343,218 B2 | 1/2013 | Lang et al. | |
| 8,366,771 B2 | 2/2013 | Burdulis, Jr. et al. | |
| 8,377,129 B2 | 2/2013 | Fitz et al. | |
| 8,382,755 B2 | 2/2013 | Austin | |
| D681,204 S | 4/2013 | Farris et al. | |
| 8,430,930 B2 | 4/2013 | Hunt | |
| 8,439,926 B2 | 5/2013 | Bojarski et al. | |
| D683,856 S | 6/2013 | Chin et al. | |
| 8,457,930 B2 | 6/2013 | Schroeder | |
| 8,460,304 B2 | 6/2013 | Fitz et al. | |
| 8,480,754 B2 | 7/2013 | Bojarski et al. | |
| 8,485,820 B1 | 7/2013 | Ali | |
| 8,500,740 B2 | 8/2013 | Bojarski et al. | |
| 8,529,568 B2 | 9/2013 | Bouadi | |
| 8,529,630 B2 | 9/2013 | Bojarski et al. | |
| D692,136 S | 10/2013 | Tyber | |
| 8,545,569 B2 | 10/2013 | Fitz et al. | |
| 8,551,099 B2 | 10/2013 | Lang et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,551,173 B2 | 10/2013 | Lechmann et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,585,708 B2 | 11/2013 | Fitz et al. | |
| 8,585,767 B2 | 11/2013 | Ullrich, Jr. et al. | |
| 8,617,172 B2 | 12/2013 | Fitz et al. | |
| 8,617,242 B2 | 12/2013 | Philipp et al. | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| D700,700 S | 3/2014 | Efinger | |
| 8,682,052 B2 | 3/2014 | Fitz et al. | |
| 8,690,945 B2 | 4/2014 | Fitz et al. | |
| 8,709,083 B2 | 4/2014 | Duffield et al. | |
| 8,709,089 B2 | 4/2014 | Lang et al. | |
| 8,715,362 B2 | 5/2014 | Reiley | |
| 8,735,773 B2 | 5/2014 | Lang | |
| D708,747 S | 7/2014 | Curran et al. | |
| 8,768,028 B2 | 7/2014 | Lang et al. | |
| 8,771,365 B2 | 7/2014 | Bojarski et al. | |
| 8,775,133 B2 | 7/2014 | Schroeder | |
| D711,537 S | 8/2014 | Pimenta et al. | |
| 8,828,311 B2 | 9/2014 | Medina et al. | |
| 8,840,668 B1 | 9/2014 | Donahoe et al. | |
| 8,843,229 B2 | 9/2014 | Vanasse et al. | |
| 8,882,847 B2 | 11/2014 | Burdulis, Jr. et al. | |
| 8,888,485 B2 | 11/2014 | Ali | |
| 8,906,107 B2 | 12/2014 | Bojarski et al. | |
| 8,926,706 B2 | 1/2015 | Bojarski et al. | |
| 8,932,363 B2 | 1/2015 | Tsougarakis et al. | |
| D722,693 S | 2/2015 | Kaufmann et al. | |
| 8,945,230 B2 | 2/2015 | Lang et al. | |
| 8,951,259 B2 | 2/2015 | Fitz et al. | |
| 8,951,260 B2 | 2/2015 | Lang et al. | |
| 8,965,088 B2 | 2/2015 | Tsougarakis et al. | |

(56) References Cited

U.S. PATENT DOCUMENTS

| | | | |
|---|---|---|---|
| D724,213 S | 3/2015 | Tyber | |
| 8,974,539 B2 | 3/2015 | Bojarski et al. | |
| 8,998,915 B2 | 4/2015 | Fitz et al. | |
| 9,020,788 B2 | 4/2015 | Lang et al. | |
| 9,023,050 B2 | 5/2015 | Lang et al. | |
| 9,034,237 B2 | 5/2015 | Sperry et al. | |
| 9,055,953 B2 | 6/2015 | Lang et al. | |
| 9,066,728 B2 | 6/2015 | Burdulis, Jr. et al. | |
| D734,460 S | 7/2015 | Froidevaux | |
| 9,072,531 B2 | 7/2015 | Fitz et al. | |
| 9,084,617 B2 | 7/2015 | Lang et al. | |
| D735,860 S | 8/2015 | Palinchik | |
| D736,384 S | 8/2015 | Palinchik | |
| 9,095,353 B2 | 8/2015 | Burdulis, Jr. et al. | |
| 9,095,439 B2 | 8/2015 | Lian | |
| 9,107,679 B2 | 8/2015 | Lang et al. | |
| 9,107,680 B2 | 8/2015 | Fitz et al. | |
| 9,113,921 B2 | 8/2015 | Lang et al. | |
| 9,125,672 B2 | 9/2015 | Fitz et al. | |
| 9,125,673 B2 | 9/2015 | Fitz et al. | |
| 9,144,500 B2 | 9/2015 | Harding | |
| 9,180,015 B2 | 11/2015 | Fitz et al. | |
| 9,180,029 B2 | 11/2015 | Hollister et al. | |
| 9,186,161 B2 | 11/2015 | Lang et al. | |
| 9,186,254 B2 | 11/2015 | Fitz et al. | |
| 9,186,257 B2 | 11/2015 | Geisler et al. | |
| D745,159 S | 12/2015 | Lin | |
| 9,216,025 B2 | 12/2015 | Fitz et al. | |
| 9,220,516 B2 | 12/2015 | Lang et al. | |
| 9,220,517 B2 | 12/2015 | Lang et al. | |
| D747,485 S | 1/2016 | Oi | |
| 9,241,724 B2 | 1/2016 | Lang et al. | |
| 9,241,725 B2 | 1/2016 | Lang et al. | |
| 9,271,845 B2 | 3/2016 | Hunt et al. | |
| 9,295,481 B2 | 3/2016 | Fitz et al. | |
| 9,295,482 B2 | 3/2016 | Fitz et al. | |
| 9,295,562 B2 | 3/2016 | Lechmann et al. | |
| 9,308,005 B2 | 4/2016 | Fitz et al. | |
| 9,308,053 B2 | 4/2016 | Bojarski et al. | |
| 9,308,060 B2 | 4/2016 | Ali | |
| 9,308,091 B2 | 4/2016 | Lang | |
| 9,308,095 B2 | 4/2016 | Parisi et al. | |
| 9,314,256 B2 | 4/2016 | Fitz et al. | |
| 9,320,620 B2 | 4/2016 | Bojarski et al. | |
| 9,326,780 B2 | 5/2016 | Wong et al. | |
| 9,333,058 B1 | 5/2016 | Krastev | |
| 9,339,279 B2 | 5/2016 | Dubois et al. | |
| 9,358,018 B2 | 6/2016 | Fitz et al. | |
| 9,364,896 B2 | 6/2016 | Christensen et al. | |
| 9,370,426 B2 | 6/2016 | Gabbrielli et al. | |
| 9,375,222 B2 | 6/2016 | Fitz et al. | |
| 9,381,025 B2 | 7/2016 | Fitz et al. | |
| 9,387,079 B2 | 7/2016 | Bojarski et al. | |
| 9,402,726 B2 | 8/2016 | Linderman et al. | |
| 9,408,615 B2 | 8/2016 | Fitz et al. | |
| 9,408,686 B1 | 8/2016 | Miller et al. | |
| 9,415,137 B2 | 8/2016 | Meridew | |
| 9,421,108 B2 | 8/2016 | Hunt | |
| D767,137 S | 9/2016 | Lin | |
| 9,433,510 B2 | 9/2016 | Lechmann et al. | |
| 9,433,707 B2 | 9/2016 | Swords et al. | |
| 9,439,767 B2 | 9/2016 | Bojarski et al. | |
| 9,486,226 B2 | 11/2016 | Chao | |
| 9,488,929 B2 | 11/2016 | Onishi | |
| 9,495,483 B2 | 11/2016 | Steines et al. | |
| 9,517,134 B2 | 12/2016 | Lang | |
| 9,545,317 B2 | 1/2017 | Hunt | |
| 9,549,823 B2 | 1/2017 | Hunt et al. | |
| 9,561,115 B2 | 2/2017 | Elahinia et al. | |
| 9,572,669 B2 | 2/2017 | Hunt et al. | |
| 9,579,110 B2 | 2/2017 | Bojarski et al. | |
| D781,422 S | 3/2017 | Hahn et al. | |
| 9,597,130 B2 * | 3/2017 | Pappalardo | A61B 17/8866 |
| 9,597,197 B2 | 3/2017 | Lechmann et al. | |
| 9,603,711 B2 | 3/2017 | Bojarski et al. | |
| 9,610,168 B2 | 4/2017 | Terrill | |
| 9,636,226 B2 | 5/2017 | Hunt | |
| 9,636,229 B2 | 5/2017 | Lang et al. | |
| 9,649,178 B2 | 5/2017 | Ali | |
| 9,662,157 B2 | 5/2017 | Schneider et al. | |
| 9,662,226 B2 | 5/2017 | Wickham | |
| 9,668,863 B2 | 6/2017 | Sharp et al. | |
| 9,675,465 B2 | 6/2017 | Padovani et al. | |
| 9,675,471 B2 | 6/2017 | Bojarski et al. | |
| 9,681,956 B2 | 6/2017 | Al Hares et al. | |
| 9,687,945 B2 | 6/2017 | Steines et al. | |
| 9,688,026 B2 | 6/2017 | Ho et al. | |
| 9,694,541 B2 | 7/2017 | Pruett et al. | |
| 9,700,420 B2 | 7/2017 | Fitz et al. | |
| 9,700,424 B2 | 7/2017 | Sanders et al. | |
| 9,700,971 B2 | 7/2017 | Lang | |
| 9,715,563 B1 | 7/2017 | Schroeder | |
| 9,737,367 B2 | 8/2017 | Steines et al. | |
| 9,750,613 B2 | 9/2017 | Petteys | |
| 9,757,235 B2 | 9/2017 | Hunt et al. | |
| 9,757,245 B2 | 9/2017 | O'Neil et al. | |
| 9,775,680 B2 | 10/2017 | Bojarski et al. | |
| 9,782,270 B2 | 10/2017 | Wickham | |
| 9,788,972 B2 | 10/2017 | Flickinger et al. | |
| 9,848,929 B2 * | 12/2017 | Dacosta | A61B 17/863 |
| 9,849,019 B2 | 12/2017 | Miller et al. | |
| 9,872,773 B2 | 1/2018 | Lang et al. | |
| 9,877,790 B2 | 1/2018 | Bojarski et al. | |
| D809,661 S | 2/2018 | Mueller et al. | |
| D813,394 S | 3/2018 | Dacosta et al. | |
| D814,037 S | 3/2018 | Dacosta et al. | |
| 9,907,670 B2 | 3/2018 | Deridder et al. | |
| 9,910,935 B2 | 3/2018 | Golway et al. | |
| 9,913,723 B2 | 3/2018 | Fitz et al. | |
| 9,918,849 B2 | 3/2018 | Morris et al. | |
| 9,925,054 B2 | 3/2018 | Siegler | |
| D814,634 S | 4/2018 | Dacosta et al. | |
| 9,943,370 B2 | 4/2018 | Asseln et al. | |
| 9,943,627 B2 | 4/2018 | Zhou et al. | |
| 9,949,839 B2 | 4/2018 | Sander | |
| 9,956,047 B2 | 5/2018 | Bojarski et al. | |
| 9,956,048 B2 | 5/2018 | Bojarski et al. | |
| 9,962,209 B2 * | 5/2018 | Dacosta | A61B 17/1615 |
| D829,909 S | 10/2018 | Horton | |
| D832,441 S | 10/2018 | Dacosta et al. | |
| 10,085,839 B2 | 10/2018 | Wong et al. | |
| D835,276 S | 12/2018 | Humphrey | |
| D835,277 S | 12/2018 | Gottlieb | |
| D835,278 S | 12/2018 | Gottlieb | |
| D835,788 S | 12/2018 | Jones et al. | |
| D835,977 S | 12/2018 | Pastorino et al. | |
| 10,183,442 B1 | 1/2019 | Miller | |
| D841,168 S | 2/2019 | Dacosta et al. | |
| 10,195,035 B1 | 2/2019 | Staton et al. | |
| 10,245,152 B2 | 4/2019 | Kloss | |
| 10,265,189 B2 | 4/2019 | Melkent et al. | |
| D849,944 S | 5/2019 | Dacosta | |
| 10,278,823 B1 | 5/2019 | Xue | |
| D850,620 S | 6/2019 | Tyber | |
| D855,184 S | 7/2019 | Predick | |
| 10,357,377 B2 | 7/2019 | Nyahay | |
| D857,201 S | 8/2019 | Predick et al. | |
| D858,769 S | 9/2019 | Barela et al. | |
| 10,449,051 B2 | 10/2019 | Hamzey | |
| D870,288 S | 12/2019 | Dang et al. | |
| 10,492,686 B2 | 12/2019 | Hunter | |
| D873,031 S | 1/2020 | Martensson | |
| D875,939 S | 2/2020 | Dacosta et al. | |
| D877,907 S | 3/2020 | Linder et al. | |
| D878,589 S | 3/2020 | Linder | |
| D878,590 S | 3/2020 | Linder et al. | |
| D879,295 S | 3/2020 | Abbasi | |
| D879,961 S | 3/2020 | Linder et al. | |
| D881,665 S | 4/2020 | Zemel et al. | |
| 10,624,746 B2 | 4/2020 | Jones et al. | |
| D884,179 S | 5/2020 | Servidio | |
| 10,667,924 B2 | 6/2020 | Nyahay | |
| 10,675,159 B2 | 6/2020 | Tipping | |
| 10,744,001 B2 | 8/2020 | Sack | |

(56)  References Cited

U.S. PATENT DOCUMENTS

| | | | |
|---|---|---|---|
| 10,772,732 B1 | 9/2020 | Miller et al. | |
| D898,197 S | 10/2020 | Cain | |
| D899,900 S | 10/2020 | Blanco | |
| D905,246 S | 12/2020 | Irwin et al. | |
| 10,898,206 B2 | 1/2021 | Dacosta et al. | |
| 10,940,015 B2 | 3/2021 | Sack | |
| D917,697 S | 4/2021 | Reed et al. | |
| D920,515 S | 5/2021 | Miller | |
| D920,516 S | 5/2021 | Miller | |
| D920,517 S | 5/2021 | Miller | |
| 11,026,798 B1 | 6/2021 | Miller | |
| 11,033,394 B2 | 6/2021 | Hamzey | |
| D925,740 S | 7/2021 | Kapitan et al. | |
| 11,135,771 B1 | 10/2021 | Reith | |
| D938,033 S | 12/2021 | Dang | |
| D942,011 S | 1/2022 | Cain | |
| D942,623 S | 2/2022 | Cain | |
| D942,624 S | 2/2022 | Cain | |
| D944,400 S | 2/2022 | Cain | |
| 11,273,048 B2 | 3/2022 | Cain et al. | |
| 11,324,525 B1 | 5/2022 | Garvey | |
| 11,353,277 B2 | 6/2022 | Muceus | |
| D962,440 S | 8/2022 | Irwin et al. | |
| 11,439,726 B2 | 9/2022 | Spence | |
| D967,960 S | 10/2022 | Wang et al. | |
| 11,471,203 B2 | 10/2022 | Sutika | |
| D968,614 S | 11/2022 | Cain | |
| D986,728 S | 5/2023 | Jou et al. | |
| 11,648,125 B2 | 5/2023 | Ng | |
| 11,666,367 B2 * | 6/2023 | Goradia | A61B 17/8888 |
| | | | 606/96 |
| 11,666,452 B2 | 6/2023 | Melkent et al. | |
| D992,116 S | 7/2023 | Miller et al. | |
| 11,744,716 B2 | 9/2023 | Jebsen et al. | |
| 11,850,144 B1 | 12/2023 | Garrigues | |
| D1,013,875 S | 2/2024 | Miller et al. | |
| D1,013,876 S | 2/2024 | Miller et al. | |
| 11,950,822 B2 * | 4/2024 | Champagne | A61B 17/848 |
| 11,960,266 B1 | 4/2024 | Kelly et al. | |
| D1,030,046 S | 6/2024 | Boey et al. | |
| D1,033,648 S | 7/2024 | Finley | |
| D1,038,400 S | 8/2024 | Kuyler et al. | |
| D1,052,732 S | 11/2024 | Pigue et al. | |
| 12,144,738 B2 | 11/2024 | Goldberg et al. | |
| 12,226,317 B2 | 2/2025 | Webb et al. | |
| D1,071,220 S | 4/2025 | Miller et al. | |
| 12,419,753 B2 | 9/2025 | White et al. | |
| 2001/0031966 A1 | 10/2001 | Tormala et al. | |
| 2003/0045834 A1 * | 3/2003 | Wing | A61B 17/3496 |
| | | | 604/161 |
| 2004/0049284 A1 | 3/2004 | German et al. | |
| 2004/0049285 A1 | 3/2004 | Haas | |
| 2004/0148032 A1 | 7/2004 | Rutter et al. | |
| 2004/0230313 A1 | 11/2004 | Saunders | |
| 2005/0010302 A1 | 1/2005 | Dietz et al. | |
| 2006/0074492 A1 | 4/2006 | Frey | |
| 2006/0229730 A1 | 10/2006 | Railey et al. | |
| 2006/0249875 A1 | 11/2006 | Robb et al. | |
| 2007/0055251 A1 | 3/2007 | Huebner et al. | |
| 2007/0100346 A1 | 5/2007 | Wyss | |
| 2007/0118243 A1 | 5/2007 | Schroeder et al. | |
| 2007/0244563 A1 | 10/2007 | Roche et al. | |
| 2008/0091271 A1 | 4/2008 | Bonitati et al. | |
| 2008/0119941 A1 | 5/2008 | Seo et al. | |
| 2008/0140214 A1 | 6/2008 | Hedley et al. | |
| 2008/0206297 A1 | 8/2008 | Roeder et al. | |
| 2008/0243260 A1 | 10/2008 | Lee et al. | |
| 2009/0062925 A1 | 3/2009 | Samuelson | |
| 2009/0093668 A1 | 4/2009 | Marten et al. | |
| 2009/0182430 A1 | 7/2009 | Tyber et al. | |
| 2010/0055644 A1 | 3/2010 | Arni | |
| 2010/0057216 A1 | 3/2010 | Gannoe et al. | |
| 2010/0076567 A1 | 3/2010 | Justin et al. | |
| 2010/0131071 A1 | 5/2010 | O'Connor et al. | |
| 2010/0137990 A1 | 6/2010 | Apatsidis et al. | |
| 2010/0168798 A1 | 7/2010 | Clineff et al. | |
| 2010/0286791 A1 | 11/2010 | Goldsmith | |
| 2011/0054611 A1 | 3/2011 | Wu et al. | |
| 2011/0106268 A1 | 5/2011 | Deffenbaugh et al. | |
| 2011/0144752 A1 | 6/2011 | Defelice et al. | |
| 2011/0190898 A1 | 8/2011 | Lenz | |
| 2011/0224796 A1 | 9/2011 | Weiland et al. | |
| 2011/0230974 A1 | 9/2011 | Musani | |
| 2011/0251614 A1 | 10/2011 | Piraino | |
| 2012/0064288 A1 | 3/2012 | Nakano et al. | |
| 2012/0215310 A1 | 8/2012 | Sharp et al. | |
| 2012/0239152 A1 | 9/2012 | Ullrich, Jr. et al. | |
| 2012/0257507 A1 | 10/2012 | Sato et al. | |
| 2012/0259419 A1 | 10/2012 | Brown et al. | |
| 2012/0323337 A1 | 12/2012 | Parisi et al. | |
| 2013/0046313 A1 | 2/2013 | Lian | |
| 2013/0068968 A1 | 3/2013 | Daniel | |
| 2013/0123935 A1 | 5/2013 | Hunt et al. | |
| 2013/0158651 A1 | 6/2013 | Hollister et al. | |
| 2013/0184820 A1 | 7/2013 | Schwartz et al. | |
| 2013/0197657 A1 | 8/2013 | Anca et al. | |
| 2013/0218282 A1 | 8/2013 | Hunt | |
| 2013/0245777 A1 | 9/2013 | Jerry | |
| 2013/0274890 A1 | 10/2013 | Mckay | |
| 2013/0296874 A1 | 11/2013 | Chao | |
| 2014/0100779 A1 | 4/2014 | Tuke | |
| 2014/0107785 A1 | 4/2014 | Geisler et al. | |
| 2014/0107786 A1 | 4/2014 | Geisler et al. | |
| 2014/0107799 A1 | 4/2014 | Tuke et al. | |
| 2014/0236299 A1 | 8/2014 | Roeder et al. | |
| 2014/0277443 A1 | 9/2014 | Fleury et al. | |
| 2014/0277452 A1 | 9/2014 | Skaer | |
| 2014/0277538 A1 | 9/2014 | Sander | |
| 2014/0288650 A1 | 9/2014 | Hunt | |
| 2014/0336680 A1 | 11/2014 | Medina et al. | |
| 2014/0350688 A1 | 11/2014 | Michel | |
| 2014/0371863 A1 | 12/2014 | Vanasse et al. | |
| 2015/0025666 A1 | 1/2015 | Olivieri et al. | |
| 2015/0045839 A1 * | 2/2015 | Dacosta | A61B 17/863 |
| | | | 606/305 |
| 2015/0045902 A1 | 2/2015 | Perler | |
| 2015/0105858 A1 | 4/2015 | Papay et al. | |
| 2015/0282945 A1 | 10/2015 | Hunt | |
| 2015/0282946 A1 | 10/2015 | Hunt | |
| 2015/0320461 A1 | 11/2015 | Ehmke | |
| 2015/0335434 A1 | 11/2015 | Patterson et al. | |
| 2015/0343709 A1 | 12/2015 | Gerstle et al. | |
| 2015/0351915 A1 | 12/2015 | Defelice et al. | |
| 2015/0374411 A1 | 12/2015 | Ehmke et al. | |
| 2016/0008139 A1 | 1/2016 | Siegler | |
| 2016/0051371 A1 | 2/2016 | Defelice et al. | |
| 2016/0089138 A1 | 3/2016 | Early et al. | |
| 2016/0151833 A1 | 6/2016 | Tsao | |
| 2016/0193055 A1 | 7/2016 | Ries | |
| 2016/0199193 A1 | 7/2016 | Willis et al. | |
| 2016/0213485 A1 | 7/2016 | Schaufler et al. | |
| 2016/0213486 A1 | 7/2016 | Nunley et al. | |
| 2016/0213487 A1 | 7/2016 | Wilson et al. | |
| 2016/0213488 A1 | 7/2016 | Moore et al. | |
| 2016/0220288 A1 | 8/2016 | Dubois et al. | |
| 2016/0228255 A1 | 8/2016 | Samuelson et al. | |
| 2016/0256279 A1 | 9/2016 | Sanders et al. | |
| 2016/0256610 A1 | 9/2016 | Zhou et al. | |
| 2016/0270920 A1 | 9/2016 | Dawson et al. | |
| 2016/0270931 A1 | 9/2016 | Trieu | |
| 2016/0287388 A1 | 10/2016 | Hunt et al. | |
| 2016/0303793 A1 | 10/2016 | Ermoshkin et al. | |
| 2016/0310189 A1 * | 10/2016 | Dacosta | A61B 17/863 |
| 2016/0333152 A1 | 11/2016 | Cook et al. | |
| 2016/0374829 A1 | 12/2016 | Vogt et al. | |
| 2017/0014169 A1 | 1/2017 | Dean et al. | |
| 2017/0018919 A1 | 1/2017 | Chen et al. | |
| 2017/0020685 A1 | 1/2017 | Geisler et al. | |
| 2017/0036403 A1 | 2/2017 | Ruff et al. | |
| 2017/0042697 A1 | 2/2017 | Mcshane, III et al. | |
| 2017/0056178 A1 | 3/2017 | Sharp et al. | |
| 2017/0056179 A1 | 3/2017 | Lorio | |
| 2017/0066873 A1 | 3/2017 | Gardet | |
| 2017/0105844 A1 | 4/2017 | Kuyler et al. | |

(56) References Cited

U.S. PATENT DOCUMENTS

| | | | |
|---|---|---|---|
| 2017/0156880 A1 | 6/2017 | Halverson et al. | |
| 2017/0165085 A1 | 6/2017 | Lechmann et al. | |
| 2017/0165790 A1 | 6/2017 | Mccarthy et al. | |
| 2017/0172758 A1 | 6/2017 | Field et al. | |
| 2017/0182222 A1 | 6/2017 | Paddock et al. | |
| 2017/0209274 A1 | 7/2017 | Beerens et al. | |
| 2017/0216035 A1 | 8/2017 | Hunt | |
| 2017/0216036 A1 | 8/2017 | Cordaro | |
| 2017/0239054 A1 | 8/2017 | Engstrand et al. | |
| 2017/0239064 A1 | 8/2017 | Cordaro | |
| 2017/0245998 A1 | 8/2017 | Padovani et al. | |
| 2017/0252165 A1 | 9/2017 | Sharp et al. | |
| 2017/0258606 A1 | 9/2017 | Afzal | |
| 2017/0282455 A1 | 10/2017 | Defelice et al. | |
| 2017/0296244 A1 | 10/2017 | Schneider et al. | |
| 2017/0319344 A1 | 11/2017 | Hunt | |
| 2017/0323037 A1 | 11/2017 | Schroeder | |
| 2017/0333205 A1 | 11/2017 | Joly et al. | |
| 2017/0354510 A1 | 12/2017 | O'Neil et al. | |
| 2017/0354513 A1 | 12/2017 | Maglaras et al. | |
| 2017/0355815 A1 | 12/2017 | Becker et al. | |
| 2017/0360488 A1 | 12/2017 | Kowalczyk et al. | |
| 2017/0360563 A1 | 12/2017 | Hunt et al. | |
| 2017/0360578 A1 | 12/2017 | Shin et al. | |
| 2017/0367843 A1 | 12/2017 | Eisen et al. | |
| 2017/0367844 A1 | 12/2017 | Eisen et al. | |
| 2017/0367845 A1 | 12/2017 | Eisen et al. | |
| 2018/0008419 A1 | 1/2018 | Tyber et al. | |
| 2018/0012517 A1 | 1/2018 | Ropelato et al. | |
| 2018/0022017 A1 | 1/2018 | Fukumoto et al. | |
| 2018/0064540 A1 | 3/2018 | Hunt | |
| 2018/0098858 A1 | 4/2018 | Valderraband | |
| 2018/0104063 A1 | 4/2018 | Asaad | |
| 2018/0110593 A1 | 4/2018 | Khalil | |
| 2018/0110626 A1 | 4/2018 | Mcshane, III et al. | |
| 2018/0110753 A1 | 4/2018 | Sack | |
| 2018/0117219 A1 | 5/2018 | Yang et al. | |
| 2018/0147319 A1 | 5/2018 | Colucci-Mizenko et al. | |
| 2018/0196920 A1 | 7/2018 | Liang et al. | |
| 2018/0256336 A1 | 9/2018 | Mueller et al. | |
| 2018/0280140 A1 | 10/2018 | Jones | |
| 2018/0289380 A1 | 10/2018 | Mauldin | |
| 2018/0289515 A1 | 10/2018 | Nemes et al. | |
| 2019/0091032 A1 | 3/2019 | Pak et al. | |
| 2019/0167433 A1 | 6/2019 | Allen | |
| 2019/0262101 A1 | 8/2019 | Shanjani et al. | |
| 2019/0269527 A1 | 9/2019 | Moore | |
| 2019/0302736 A1 | 10/2019 | Chanin | |
| 2019/0343652 A1 | 11/2019 | Petersheim et al. | |
| 2020/0000595 A1 | 1/2020 | Jones | |
| 2020/0030102 A1 | 1/2020 | Mullens et al. | |
| 2020/0030108 A1 | 1/2020 | Orphanos et al. | |
| 2020/0046512 A1 | 2/2020 | Newman et al. | |
| 2020/0085452 A1 | 3/2020 | Siegler | |
| 2020/0085585 A1 | 3/2020 | Siegler | |
| 2020/0107934 A1 | 4/2020 | Pontius | |
| 2020/0107940 A1 | 4/2020 | Murphy et al. | |
| 2020/0155321 A1 | 5/2020 | Dikovsky | |
| 2020/0171752 A1 | 6/2020 | Rogren | |
| 2020/0171753 A1 | 6/2020 | Satko | |
| 2020/0253649 A1 | 8/2020 | Langdale et al. | |
| 2020/0367910 A1 | 11/2020 | Hafez et al. | |
| 2021/0000588 A1 | 1/2021 | Cain | |
| 2021/0077276 A1 | 3/2021 | Garvey et al. | |
| 2021/0110605 A1 | 4/2021 | Haslam et al. | |
| 2021/0113222 A1 | 4/2021 | Khatibi et al. | |
| 2021/0121298 A1 | 4/2021 | Walker et al. | |
| 2021/0216683 A1 | 7/2021 | Rai | |
| 2021/0298908 A1 | 9/2021 | Holmes | |
| 2021/0307765 A1 | 10/2021 | Dumpe et al. | |
| 2021/0340334 A1 | 11/2021 | Portela | |
| 2022/0023048 A1 | 1/2022 | Nolens | |
| 2022/0087670 A1 | 3/2022 | Selmoune | |
| 2022/0134639 A1 | 5/2022 | Allen | |
| 2022/0142783 A1 | 5/2022 | Ahmadi | |
| 2022/0168109 A1 | 6/2022 | Giordano | |
| 2022/0226094 A1 | 7/2022 | Chotkowski et al. | |
| 2022/0296386 A1 | 9/2022 | Fang | |
| 2022/0401138 A1 | 12/2022 | Finley et al. | |
| 2023/0114676 A1 | 4/2023 | Harris et al. | |
| 2023/0122922 A1 | 4/2023 | Daudet | |
| 2023/0190492 A1 | 6/2023 | Marks et al. | |
| 2024/0033092 A1 | 2/2024 | Parthasarathy et al. | |
| 2024/0065767 A1 | 2/2024 | Cordonnier et al. | |
| 2024/0245523 A1 | 7/2024 | Mermuys et al. | |
| 2024/0374291 A1 | 11/2024 | Ogilvie et al. | |
| 2025/0099255 A1 | 3/2025 | Hintermann et al. | |
| 2025/0152095 A1 | 5/2025 | Hunter | |

FOREIGN PATENT DOCUMENTS

| | | |
|---|---|---|
| CN | 110090096 | 8/2019 |
| CN | 306895697 S | 10/2021 |
| DE | 69806985 | 6/2003 |
| EP | 1180989 | 4/2006 |
| EP | 2832321 | 2/2015 |
| EP | 2635239 | 7/2017 |
| EP | 2913030 | 3/2018 |
| EP | 3586800 | 1/2020 |
| FR | 026681-002 S | 2/2003 |
| FR | 3071400 | 3/2019 |
| GB | 4005303 S | 2/2008 |
| JP | 4840886 | 12/2011 |
| KR | 300766315 S | 10/2014 |
| KR | 301007894 | 5/2019 |
| WO | 2014020561 A1 | 2/2014 |
| WO | 2014020562 | 2/2014 |
| WO | 2015054070 A1 | 4/2015 |
| WO | 2020123295 A1 | 6/2020 |
| WO | D211856-003 S | 1/2021 |
| WO | 2023183793 A2 | 11/2023 |

OTHER PUBLICATIONS

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).

Rozema et al., The effects of different steam-sterilization programs on material properties of poly(I-lactide), Journal of Applied Biomaterials, vol. 2, 23-28 (1991) (Year: 1991).

Alt, Sami. "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 30 Printed Polycarbonate Urethane in Solution, 108 Polymer 121 (2017).

Andrew T. Miller et al., Deformation and Fatigue of Tough 30 Printed Elastomer Scaffolds Processed by Fused 3 Deposition Modeling and Continuous Liquid Interface Production, 75 J. Mechanical Behavior Biomedical Materials 1 (2017).

Ortho Spine News, "SeaSpine Announces 25,000th NanoMetalene Implantation", first available Dec. 18, 2019. (https://orthospinenews.com/2019/12/18/seaspine-announces-25000th-nanometalene-implantation/) (Year: 2019).

Restor3d, "Products", first available Sep. 28, 2020. (https://web.archive.org/web/20200928123335/https:/restor3d.com/ products) (Year: 2020).

Ortho Spine News, "Nvision Biomedical Technologies: First FDA Clearance for Osteotomy Wedge System", first available Oct. 28, 2020. (https://orthospinenews.com/2020/10/28/nvision-biomedical-technologies-first-fda-clearance-for-osteotomy-wedge-system-made-of-peek-optima-ha-enhanced/) (Year: 2020).

Sina, "Application logic of triple periodic minimum surface", first available Oct. 24, 2020. (https://k.sina.com.cn/article_2422410454_90630cd6001 OOtlbm.html?from=science) (Year: 2020).

(56) References Cited

OTHER PUBLICATIONS

3D Adept Media, "Johnson & Johnson Medical", first available Sep. 17, 2018. (https://3dadept.com/johnson-johnson-medical-has-acquired-3d-printed-spmplants-special ist-emerging-implant-technologies/) (Year: 2018).

Additive Orthopaedics, "Additive Orthopaedics 3d Printed Cotton Bone Segment", first available Sep. 19, 2020. (https://web.archive.org/web/20200919145251/https://www.additiveorthopaedics.com/our-products/cotton/) (Year: 2020).

Indiamart, "Anterior Cervical Fusion Cage for Spine Surgery", first accessed Dec. 9, 2020. (https://www.indiamart.com/proddetail/ anterior-cervical-fusion-cage-12402896897 .html) (Year: 2020).

Instagram, "restor3d", first available Jul. 21, 2020. (https://www.instagram.com/p/CC6dztOAKcM/?utm_source=ig_web_link) (Year: 2020).

Yan et al., "Ti-6Al-4V triply periodic minimal surface structures for bone implants fabricated via selective laser melting", Jul. 9, 2015, Journal of the mechanical behavior of biomedical materials 51 (2015), 61-73 (Year: 2015).

Yan et al., "Microstructure and mechanical properties of aluminum alloy cellular lattice structures manufactured by direct metal laser sintering", Jan. 31, 2015, Materials Science and Engineering A 628 (2015), 238-246 (Year: 2015).

Cera-Metal orthopedic implant coating, ifdesign.com, Published 2006 , Accessed Jul. 24, 2024, https://ifdesign.com/en/wi nner-ranking/projecUcera-metal/27188.

Does 3D Printing Add Value in Orthopedics?, publication date Apr. 1, 2019, https://www.odtmag.com/issues/2019-04-01 /view_features/ does-3d-printing-add-value-in-orthopedics/.

[MTP Hemiarthroplasty Implant Featuring TIDAL Technology™], cdn.prod.website-files.com, Posted: Mar. 2023 [online], site visited: [Jul. 25, 2024], URL: <https://cdn.prod. website-files.com/ 65d612f03cc5c490660ab482/65d612f03cc5c490660ab 7 aa_restor3d-MTP-Sales-Sheet. pdf>. (Year: 2023).

3D printing implants: A complete guide, publication date Feb. 1, 2023, https://www.ntop.com/resources/blog/3d-printing-implants-a-complete-guide/.

Cotton Wedge Portfolio, cdn.prod.website-files.com, Published Jun. 1, 2023, Accessed Jul. 25, 2024, URL: https://cdn.prod.website-files.com/65d612f03cc5c490660ab482/65d612f03cc5c490660ab7bd_ MKG-010%20 REV01%20JUN2023%20Wedge%20Portfolio% 20Brochure.pdf (Year: 2023).

3D Printing for Orthopedic Implant, https://www.eplus3d.com/3d-printing-for-orthopedic-implant.html, Accessed Jan. 8, 2025.

Apex 3D Total Ankle Replacement, Paragon 28, Retrieved from internet: https://paragon28.com/app/uploads/2021/08/DIGITAL-P10-STM-0001-Rev-A_APEX_TAR_SystemOverview.pdf, 2020, 8 pages.

Foot and Ankle Wedge Portfolio with TIDAL Technology™, restor3d, URL: https://www.restor3d.com/wp-content/uploads/2024/07/Foot-Ankle-Wedge-Portfolio-Brochure.pdf, 2023, 2 pages.

Inbone Total Ankle System, Stryker, Retrieved from internet, https:// www.stryker.com/content/dam/stryker/foot-and-ankle/products/inbone/ resources/Inbone-Brochure.pdf, 2022, 6 pages.

Kinos Total Ankle System, restor3d, Retrieved from internet: https:// www.restor3d.com/healthcare-professionals/products/foot-ankle/ total-ankle-replacement/, 2023, 5 pages.

Restor3d | Choose Your Motion, Instagram posted Oct. 3, 2024, Retrieved from internet, https://www.instagram.com/restor3d/p/ DArDUCLSoCj/?img_index=1, 1 page.

Rose, "Paragon 28, Inc. is pleased to announce that the U.S. Food and Drug Administration has cleared the Apex 3D™ Total Ankle Replacement System", P28 News, Retrieved from internet, https:// paragon28.com/paragon-28-inc-is-pleased-to-announce-that-the-u-s-food-and-drug-administration-has-cleared-the-apex-3d-total-ankle-replacement-system/, Jul. 15, 2020, 1 page.

TIDAL™ Subtalar Wedge System, restor3d, retrieved from: https:// www.restor3d.com/wp-content/uploads/2024/07/TIDAL@-Subtalar-Wedge-System-Surgical-Technique.pdf, 2022, 10 pages.

Trabecular Metal Total Ankle, Zimmer, Retrieved from internet: https://www.zimmerbiomet.com/content/dam/zb-corporate/en/products/ specialties/foot-&-ankle/trabecular-metal-total-ankle-system/ zimmertrabecularmetaltotalanklebrochure.pdf, 2013, 6 pages.

Vantage Total Ankle, exactech , Retrieved from internet, https:// www.exac.com/wp-content/uploads/2024/09/721-00-10_Rev_D_ Exactech_Vantage_Ankle_Product_Sheet_US_Web.pdf, 2024, 2 pages.

* cited by examiner

INSTRUMENTS AND METHOD FOR ANKLE REPLACEMENT SURGERY

INCORPORATION BY REFERENCE

This application is a divisional of U.S. patent application Ser. No. 17/025,151, filed on Sep. 18, 2020, entitled "INSTRUMENTS AND METHOD FOR ANKLE REPLACEMENT SURGERY," which claims the priority of U.S. Provisional Patent Application 62/902,181, filed Sep. 18, 2019, entitled "INSTRUMENTS AND METHOD FOR ANKLE REPLACEMENT SURGERY," each of which are each incorporated herein by reference in their entireties.

FIELD OF INVENTION

The present disclosure relates to tools and methods for performing ankle replacement surgery.

BACKGROUND

Ankle replacement surgery is a procedure for treating patients with end stage ankle arthritis, rheumatoid arthritis and other painfully arthritic conditions of the ankle or other maladies. Total ankle replacement (TAR), as it is commonly referred to, is typically not as clinically successful as other total joint replacements (i.e. knee, hip, shoulder). The failure rates of TAR procedures are sometimes two or three times greater than total knee or total hip replacement.

One of the more difficult aspects of a TAR procedure is manually aligning the patient's ankle joint so that the surgeon may make the appropriate bone resection cuts. The location and accuracy of the bone resection cuts determine the location of the total ankle implant and ultimately determine how well the implant will function and to what extent the patient's quality of life has improved. Accordingly, making accurate incisions is critical to a successful surgery and recovery.

The ankle joint must be appropriately aligned with long axis of the tibial bone in order to place the implant where it will most effectively provide the requisite range of motion and counteract the forces experienced in daily activities, such as walking, jogging, standing, etc. There are six degrees of freedom that must be aligned by the surgeon during the surgery. The alignment of the ankle joint is achieved with instruments used to prepare the tibial and talar bones in preparation of implant placement.

It would be desirable to provide instruments and tools that ensure surgeons and other medical personnel can perform reliable and accurate alignment of a patient's ankle joint prior to and during surgery.

SUMMARY

The present disclosure generally discloses instruments and methods of using those instruments for performing various aspects of ankle replacement surgery.

In one embodiment, an instrument and method of adjusting two degrees of freedom is provided. The instrument contains a linkage that is positioned specifically to allow the surgeon to adjust *varus* and valgus angular position of the instrument relative to the patient's anatomy. In one embodiment, these adjustments are made between +75° and −75° from a line perpendicular to a longitudinal axis of the tibial bone.

In one embodiment, another linkage and method of using the linkage is provided. The linkage is positioned specifically to allow the surgeon to adjust the opening angle (commonly referred to as "slope") of the instrument relative to the patient's anatomy. In one embodiment, both of these linkages utilize a screw or gear type feature that actuates the adjustment assembly, causing rotation about a fixed point, thereby adjusting the relative angle between the instrument and the bone. In one embodiment, these adjustments are made between +45° and −45° from a line perpendicular to the long axis of the tibial instrument. The alignment guide permits these adjustments and reduces the likelihood of misalignment and improves a surgeon's ability to precisely select an angle most appropriate for the patient.

An alignment assembly for adjusting a position of a guide tool relative to a patient is disclosed herein. The alignment assembly includes a proximal housing; a distal housing configured to be connected to the guide tool; and at least one linkage system configured to adjust a relative angle between the proximal housing and the distal housing.

In one aspect, the at least one linkage system includes a first linkage system and a second linkage system, and the first linkage system is oriented 90 degrees relative to the second linkage system such that the first and second linkage systems provide angulation about two different axes.

In another aspect, the first linkage system and the second linkage system each translate rotational input motion to linear output motion.

The relative angle is adjusted between +75° and −75° from a neutral position defined along a line extending parallel to the longitudinal axis of the tibia.

An intermediate housing can be positioned between the proximal housing and the distal housing in one embodiment.

In one embodiment, the first angular adjustment shaft includes a first threading and extends through a first linkage shaft having a second threading configured to engage with the first threading, and rotational motion applied to the first angular adjustment shaft drives the first linkage shaft linearly along the first angular adjustment shaft such that distal housing and the proximal housing pivot relative to each other in a first angular direction. The second angular adjustment shaft includes a third threading and extends through a second linkage shaft having a fourth threading configured to engage with the third threading, and rotational motion applied to the second angular adjustment shaft drives the second linkage shaft linearly along the second angular adjustment shaft such that distal housing and the proximal housing pivot relative to each other in a second angular direction.

A height adjustment assembly can be provided to adjust a relative height between the proximal housing and the distal housing.

In one aspect, a single tool can be configured to engage the first angular adjustment shaft and the second angular adjustment shaft, and the single tool is configured to rotationally engage both the first angular adjustment shaft and the second angular adjustment shaft.

In another embodiment, a surgical guide wire is provided. The wire includes: a distal tip having a tapered or trocar end configured for insertion into a bone; a distal region adjacent to the distal tip, the distal region being configured to be partially inserted into the bone; a transition region adjacent to the distal region, the transition region including a portion with a smaller diameter than a diameter of the distal region; and a proximal region adjacent to the transition region.

In one embodiment, at least a portion of the transition region has a diameter that is less than 75% of a diameter of the distal region. In another embodiment, the transition region is positioned at least ¼-⅓ of a total length of the guide wire away from the distal tip.

The transition region can have a tapered profile, with a larger end connected to the distal region and a smaller end connected to the proximal region.

The transition region can have a uniform profile having a smaller diameter than the proximal region or the distal region, a first connection portion between the transition region and the proximal region having a first tapered profile, and a second connection portion from the transition region to the distal region having a second tapered profile. The first tapered profile can be different than the second tapered profile.

Other embodiments are disclosed herein.

BRIEF DESCRIPTION OF THE DRAWINGS

The foregoing Summary and the following Detailed Description will be better understood when read in conjunction with the appended drawings, which illustrate a preferred embodiment of the invention. In the drawings.

DETAILED DESCRIPTION OF THE PREFERRED EMBODIMENTS

Figure 1:
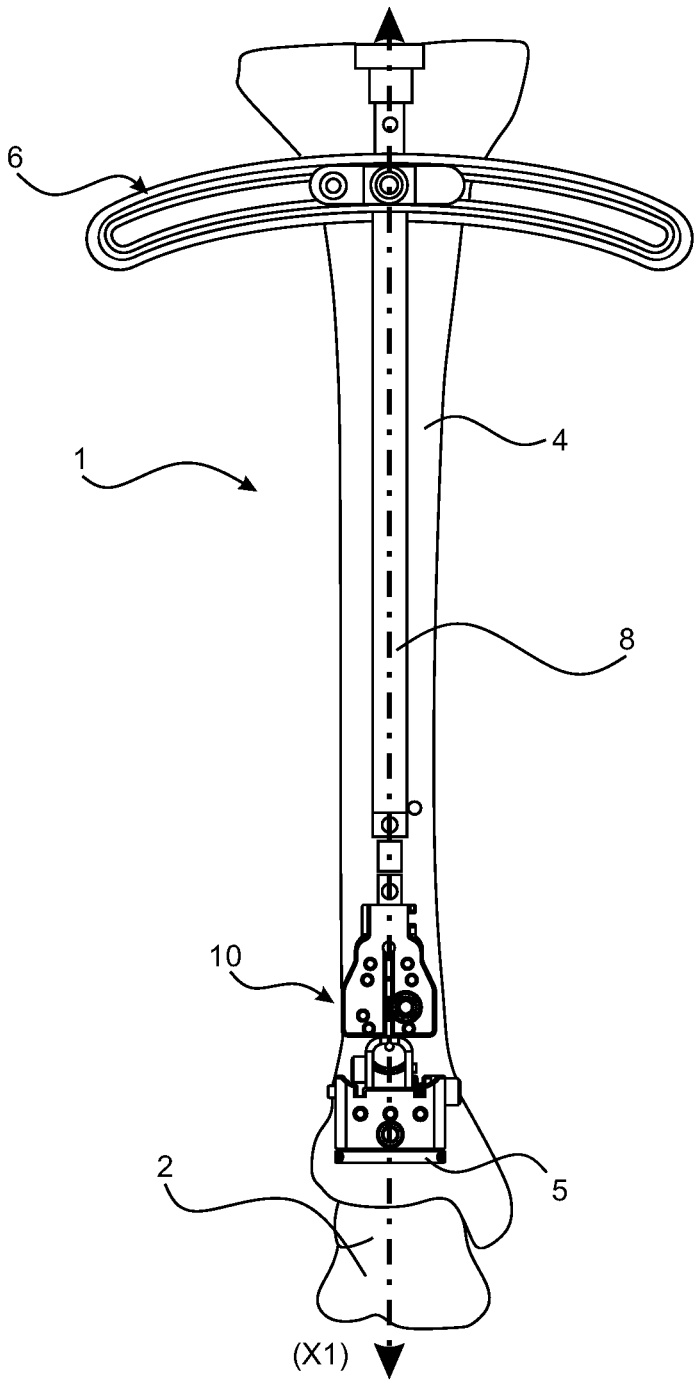
FIG. 1 is a view of an instrument according to this disclosure positioned relative to a patient's tibia and talus.

Instruments are disclosed herein that aid with adjusting the *varus*-valgus alignment, and adjusting the opening angle (i.e. slope) alignment. The *varus*-valgus adjustment is a rotational adjustment of the instruments relative to the longitudinal axis of the tibial bone when viewed in a coronal plane. This adjustment allows the surgeon to specify the coronal plane angulation of the bone cut required to place the implant, thereby specifying the coronal plane angulation of the tibial implant relative to the tibial bone. The slope adjustment is a rotational adjustment of the instruments relative to the longitudinal axis of the tibial bone when viewed in a sagittal plane. This adjustment allows the surgeon to specify the sagittal plane angulation of the bone cut required to place the tibial implant, thereby specifying the sagittal plane angulation of the tibial implant relative to the tibial bone. These instruments are intended to be used to implant any one or more of a tibial implant, a talar implant, or a bearing implant. One of ordinary skill in the art would understand that the tools can be used to align tools for other activities.

The description herein refers generally to tools and instruments for performing adjustments and alignments. One of ordinary skill in the art would understand that a corresponding method of using these tools and instruments are also within the scope of this disclosure.

In general, total ankle replacement surgery requires that a patient is placed supine on an operating table support. A protrusion or bump can be placed under the patient's calf to maintain proper rotation of the patient's leg. The patient's patella is arranged to face directly anterior. General or regional anesthesia may be used. If using regional anesthesia, the sciatic or popliteal catheter must be positioned in a way that does not interfere with the surgery. A thigh tourniquet is generally used proximal to the popliteal catheter. Intravenous antibiotics and sequential compression are used on the contralateral leg. The leg is prepared and draped using proper sterile technique, leaving the knee to foot exposed. Exsanguination is performed prior to tourniquet activation.

A skin incision is made just lateral to the tibial crest from approximately 6 cm proximal of the tibial plafond, and extending distal up to the talonavicular joint. The superficial peroneal nerve is identified and mobilized laterally. The extensor retinaculum and EHL tendon sheath are exposed, but the anterior tibial tendon sheath cannot be exposed. The deep peroneal nerve and artery are then identified and mobilized laterally. It is important to protect these structures throughout the procedure. Finally, the ankle joint capsule is incised longitudinally and exposed from the medial malleolus to the syndesmosis. Osteophytes on the neck of the talus and anterior tibia must be removed. It is important to avoid weakening the underlying bone by removing too much substrate. If a *varus* deformity requires correction, a deltoid release is performed. It is important to release the talar deltoid attachment from anterior to posterior as a single structure. As explained above, these surgeries and procedures are complicated and require that surgeons can correctly, accurately, and precisely have access to specific portions of the patient's anatomy. Accordingly, the subject matter disclosed herein provides an improved tool, process, and method of aligning surgical instruments and tools relative to a patient.

In one aspect, an instrument is generally disclosed herein for aligning a secondary tool (such as a bone manipulation guide) relative to a patient. The instrument includes a least one linkage system configured to adjust an angular alignment of the tool. This instrument is particularly configured to be used during ankle replacement surgery. In one aspect, the angular adjustments are between +75° and −75° from a neutral position (such as a line perpendicular to a longitudinal axis of the instrument). In one aspect, the linkage system comprises a rotating a shaft configured to rotate within an intermediate housing. The linkage system generally translates rotational motion to linear motion in one aspect. The intermediate housing may pivot relative to the proximal housing through a common point or pivot axis between the proximal housing and the linkage system.

The term secondary tool is used broadly herein to refer to any surgical tool. Specifically, the term secondary tool can refer to at least a bone manipulation guide, a saw cut guide, a k-wire guide, a broach guide, or drill guide.

The at least one linkage system includes two linkage systems in one embodiment. The two linkage systems are oriented 90 degrees relative to each other to provide angulation about two axes. In one embodiment, the angulation adjustments correspond to a coronal plane adjustment and a sagittal plane adjustment.

Referring to the drawings, an instrument 1 is provided for adjusting at least two of the degrees of freedom. FIG. 1 illustrates the instrument 1 relative to a patient's talus 2 and a patient's tibia 4. The instrument 1 generally includes a shaft alignment tool 6 that is configured to adjust a shaft 8 of the instrument relative to an axis of the tibia 4. A proximal end of the shaft 8 is attached to an adjustment assembly 10. The shaft 8 provides a reference of the instrument 1 that the surgeon may approximately align with the longitudinal axis of the patient's tibial bone in both the coronal and sagittal planes. In one example, the surgeon will provisionally align the shaft 8 to be parallel to the longitudinal axis of the patient's tibial bone in both the coronal and sagittal planes.

Regarding the adjustment assembly 10, this feature is generally provided to allow a surgeon to adjust angular positions of the instrument 1 relative to a patient's anatomy. In one aspect, the adjustments are *varus* and valgus adjustments. In one aspect, the adjustments provided by the adjustment assembly 10 are made between +75° and −75° from a line perpendicular to a longitudinal axis (X1) of the instrument 1, which is parallel to a longitudinal axis of the tibia 4.

Figure 2:
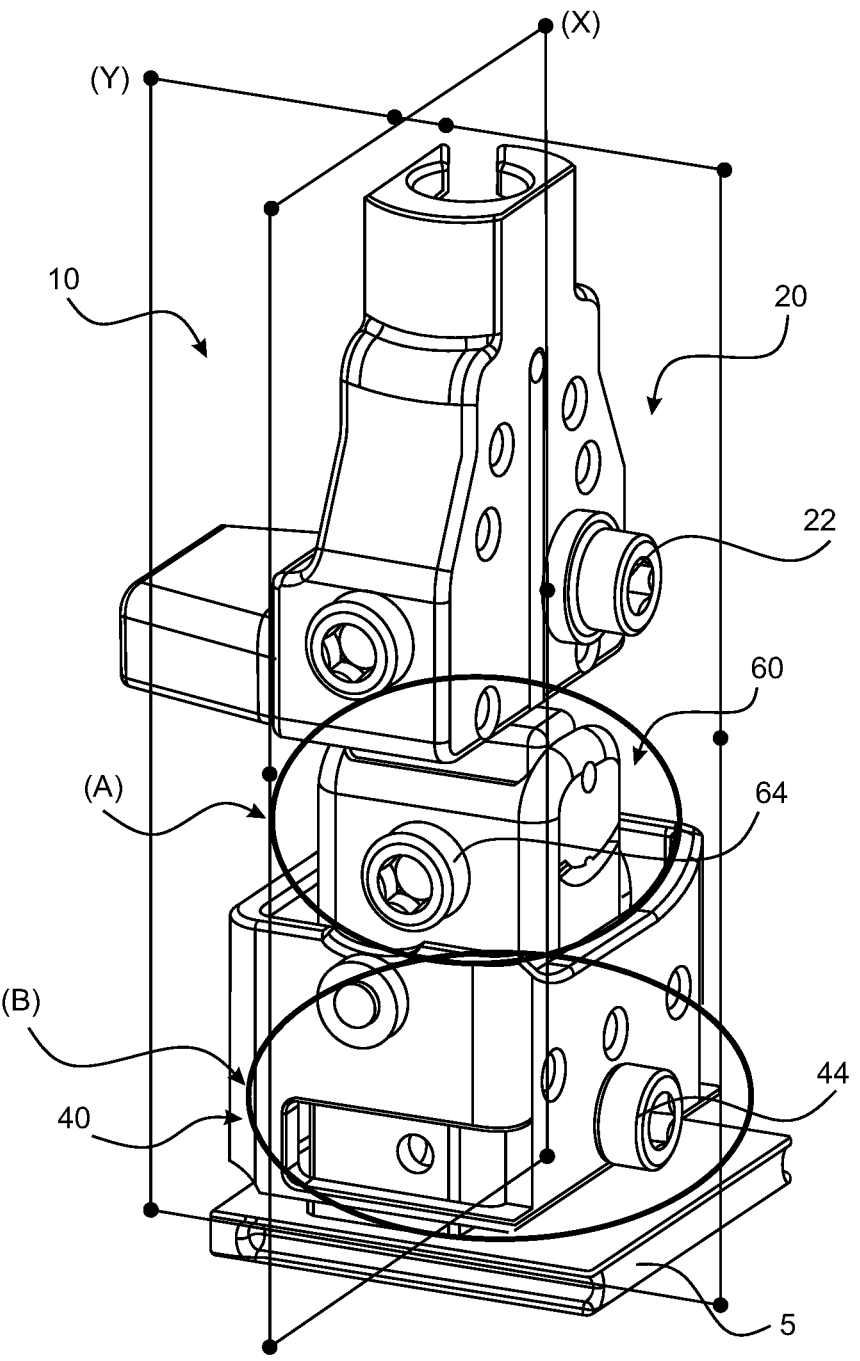
FIG. 2 is a perspective view of the instrument of FIG. 1.

The adjustment assembly 10 is shown in more detail in FIG. 2. As shown in FIG. 2, the adjustment assembly 10 includes a first or proximal housing 20 and a second or distal housing 40. At a high level, the proximal housing 20 and the distal housing 40 are adjustable relative to each other, and a carriage 45 of the distal housing 40 are adjustable relative to each other. In one aspect, the proximal housing 20 and the distal housing 40 are adjustable relative to each other via an intermediate housing 60.

Figure 4:
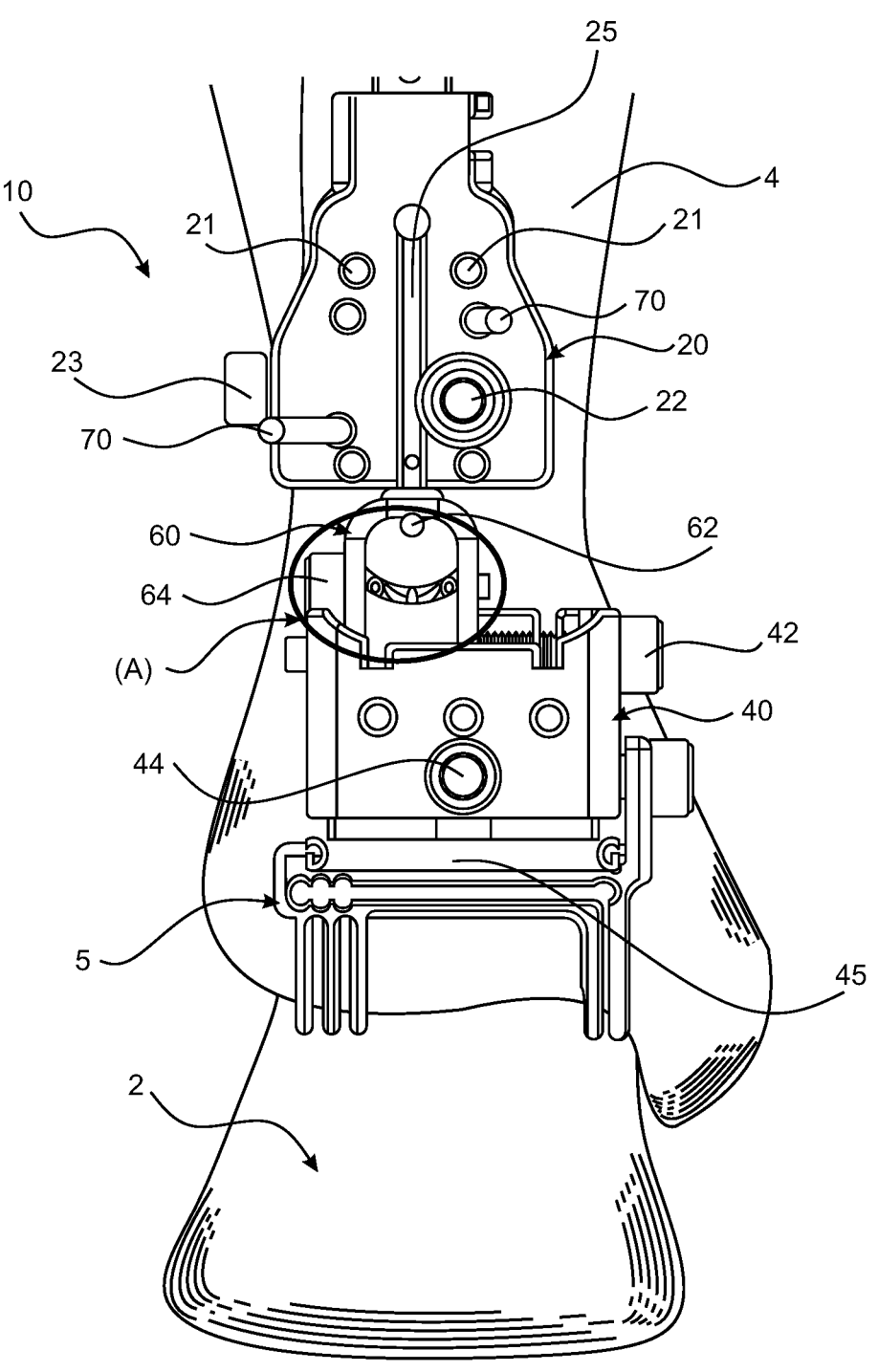
FIG. 4 is a side view of the instrument.

The proximal housing 20 includes a plurality of openings 21 which define through holes generally oriented towards the patient's anatomy. As shown in FIG. 4, at least two of the openings 21 are occupied by guide wires 70. As used herein, the term guide wires 70 generically refers to any cylindrical rod or wire that aids in attaching the instruments relative to the patient's anatomy. For example, the guide wires 70 can be a Kirschner wire or K-wire. As shown in FIG. 4, these wires 70 are generally provided to maintain alignment of the instrument and fix a position of the proximal housing 20 relative to the patient's anatomy, and more specifically relative to the tibia 4.

The proximal housing 20 can include a height adjustment assembly 22. The term height is used to refer a dimension in the longitudinal or vertical direction, i.e. the up and down direction shown in FIG. 4. The height adjustment assembly 22 can include a gear that is manually turned to adjust a relative height between the proximal housing 20 and the distal housing 40. The height can be freely adjustable in an up or down direction via the height adjustment assembly 22. Once a desired relative vertical or longitudinal distance is set between the proximal housing 20 and the distal housing 40, then a locking assembly 23 can be actuated to fix the relative distance between the proximal housing 20 and the distal housing 40. As shown in FIG. 4, an adjustment knob of the height adjustment assembly 22 is generally oriented in the same direction as the plurality of openings 21, and an axis of the locking assembly 23 is oriented perpendicular to the adjustment knob of the height adjustment assembly 22. One of ordinary skill in the art would understand that the orientation of these components can vary.

Figure 5:
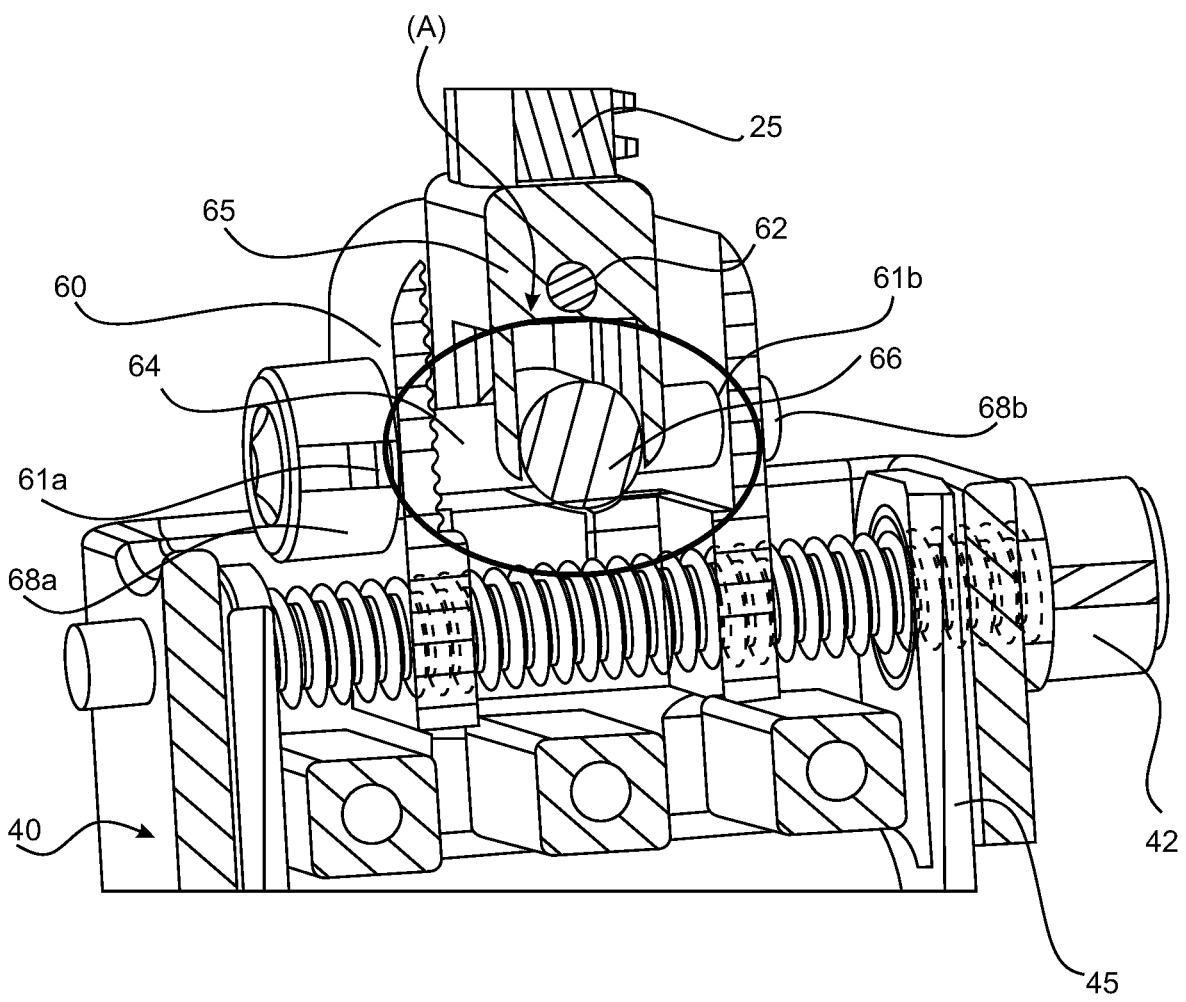
FIG. 5 is a cross-sectional view of the instrument in a medial section.
Figure 7:
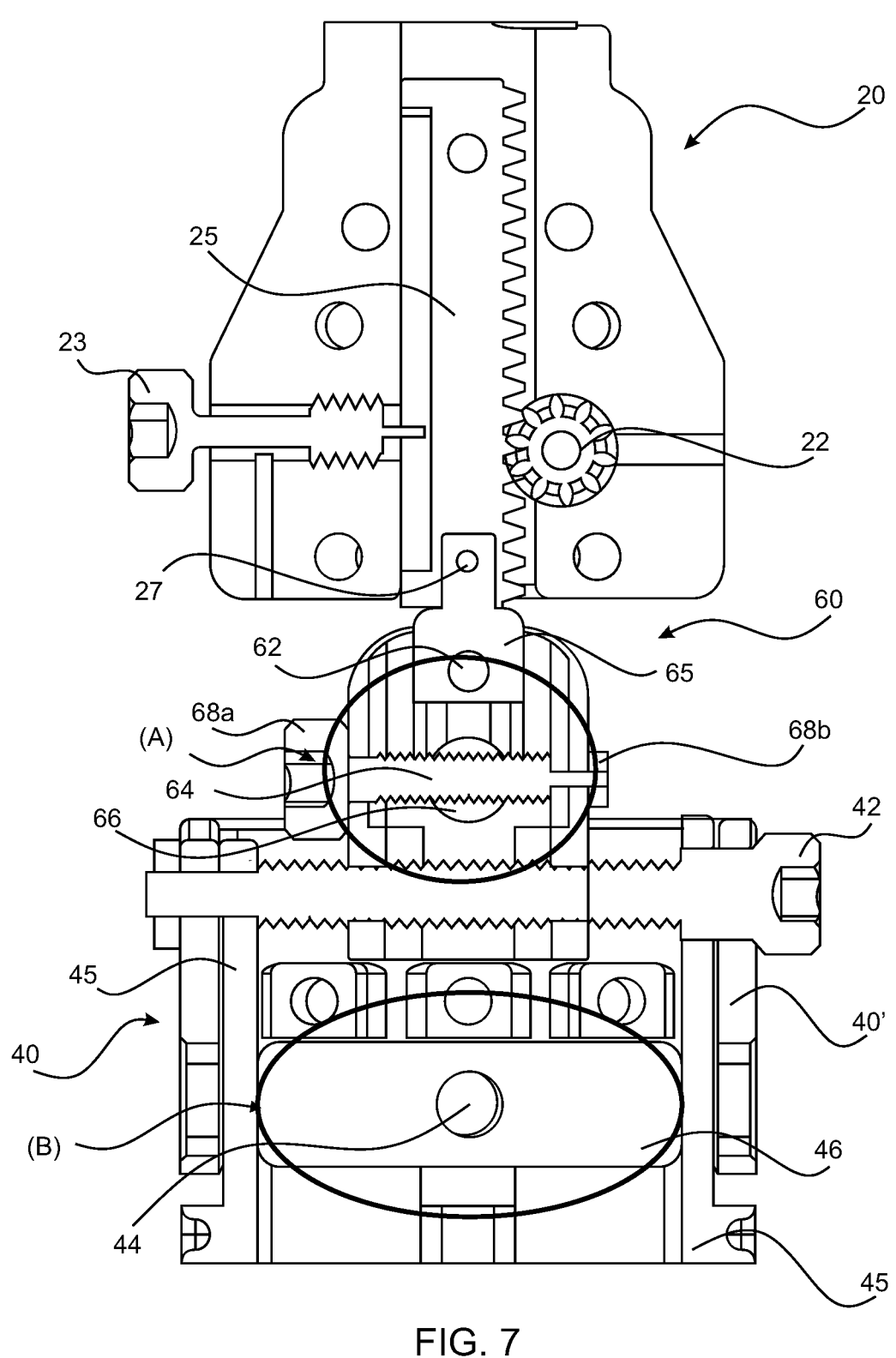
FIG. 7 is another cross-sectional view of the instrument.
Figure 8:
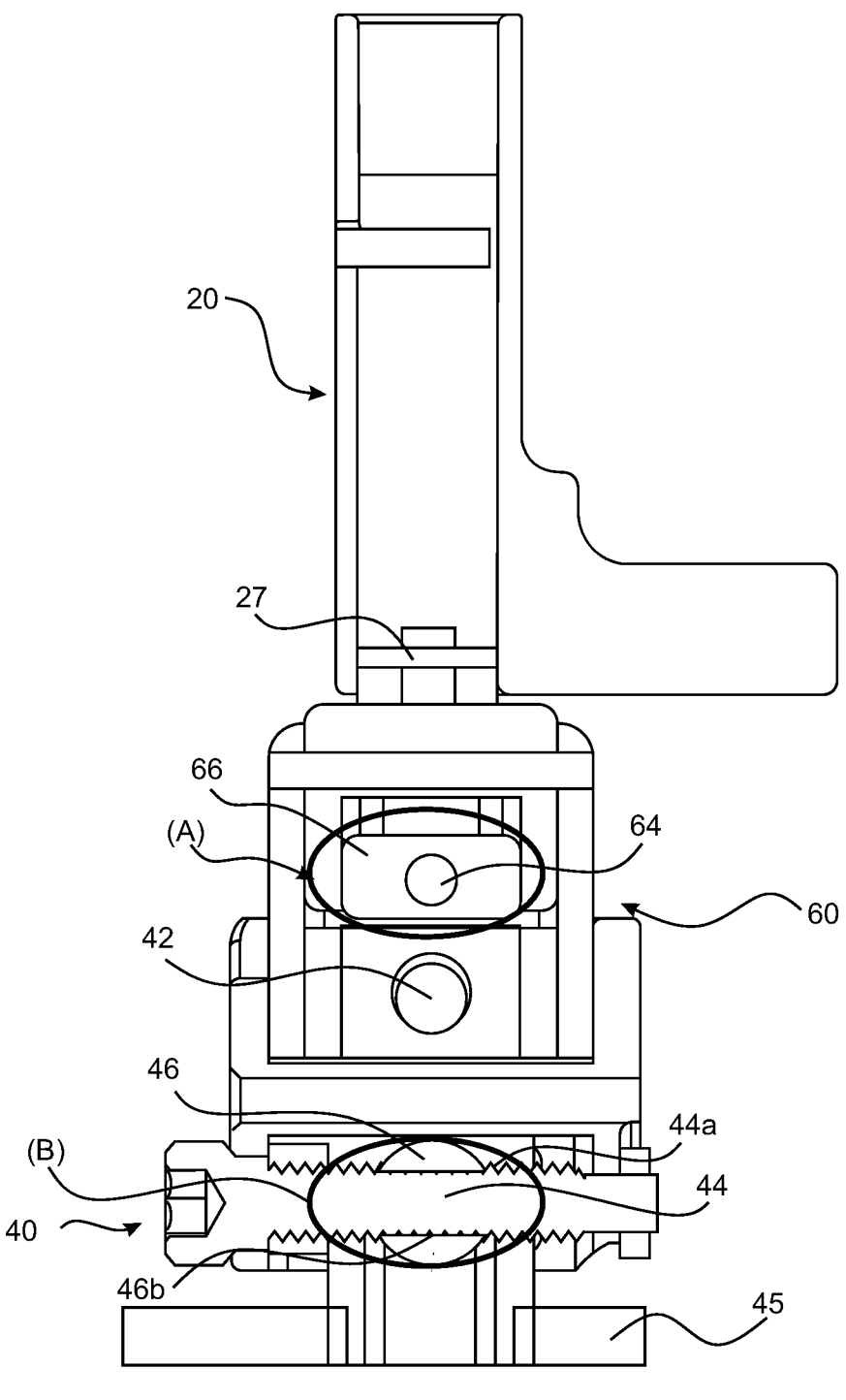
FIG. 8 is another cross-sectional view of the instrument.

As shown in FIGS. 4 and 5, the height adjustment assembly 22 also includes a shaft 25 that is connected to a linkage block 65. The shaft 25 is adjustable by engaging the height adjustment assembly 22, which is illustrated as a gear or screw in FIG. 4. As shown in FIGS. 7 and 8, a pin 27 is provided that connects the shaft 25 to the linkage block 65.

The proximal housing 20 is pivotally attached to the intermediate housing 60. In one embodiment, as shown in FIG. 4, a pin 62 provides a pivoting arrangement between the proximal housing 20 and the intermediate housing 60. The pin 62 provides an axis of revolution between the angle adjustment of the proximal housing 20 relative to the intermediate housing 60.

As shown at a high level in FIG. 2, the adjustment assembly 10 generally provides at least two linkage systems A, B. The linkage systems A, B are configured to provide angular adjustment in two different directions. In one embodiment, the two different directions are oriented perpendicular or 90 degrees relative to each other. A first angular adjustment shaft 64 is provided for the first linkage system A, and a second angular adjustment shaft 44 is provided for the second linkage system B. Specific details for the shafts 44, 64 and the other components engaged by the shafts 44, 64 are described in detail herein. However, the scope of this disclosure covers any type of interface arrangement that provides for a manually adjustable feature (i.e. the shafts 44, 64) and the ability to apply an impulse or action to the shaft such that the adjustment assembly 10 is adjusted in two directions. Various features of the threadings, the linkage shafts, etc. can be modified or omitted such that the same resulting angulation is achieved. In other words, one of ordinary skill in the art would understand that modifications to the linkage systems A, B can be implemented to achieve the same result of having an adjustment assembly 10 with at least two angulation adjustment features.

Generally, as the first angular adjustment shaft 64 is engaged or actuated (i.e. rotated), then an articulation angle between the proximal housing 20 and the distal housing 40 is adjusted. As shown in FIG. 2, as the first angular adjustment shaft 64 is actuated, the proximal housing 20 or the distal housing 40 will be pivoted in the coronal plane (X). As shown in FIG. 2, as the second angular adjustment shaft 44 is actuated, then another articulation angle between the proximal housing 20 and the distal housing 40 is adjusted, and the proximal housing 20 or the distal housing 40 will be pivoted in the sagittal plane (Y). Generally, the proximal housing 20 will be fixed to a patient during this adjustment stage, and therefore the distal housing 40 generally will be the mobile component that is driven during these adjustments. However, one of ordinary skill in the art would understand that relative positions of either housing 20, 40 can be adjusted.

The first angular adjustment shaft 64 is included with the intermediate housing 60. As used herein, the term angular adjustment shaft can refer to any screw, gear, bolt, threaded rod, etc. that is configured to be actuated to adjust an angular position between two components. The first angular adjustment shaft 64 is configured to be actuated, e.g. by a surgeon possibly using a tool, which adjusts a relative angle between the proximal housing 20 and the distal housing 40. In one aspect, the adjustment carried out by the first angular adjustment shaft 64 is completely independent of any height adjustment between the proximal housing 20 and the distal housing 40.

As shown in FIG. 2, a shaft 42 extends laterally though the distal housing 40. This shaft 42 generally connects the distal housing 40 to the intermediate housing 60. The shaft 42 also links a carriage 45 of the distal housing 40 to the intermediate housing 60. As shown in FIG. 7, the shaft 42 includes a smooth bearing surface in a region of the linkage 45, and an outer housing 40' of the distal housing 40. The shaft 42 includes threading to connect with the intermediate housing 60. The shaft 42 allows for pivoting or rotational movement between the distal housing 40 and the intermediate housing 60 due to the shaft 42 lacking any threading in an area of connection with the distal housing 40 or an outer housing 40' of the distal housing 40. The shaft 42 can include an enlarged head and/or locking washers on its axial ends to retain the shaft relative to the distal housing 40.

As shown in FIG. 2, a secondary instrument 5 can be provided. This secondary instrument 5 is shown as a guide tool that is configured to assist surgeons with drilling, cutting, inserting, and other actions associated with performing joint replacement surgeries. For example, the secondary instrument 5 can aid surgeons with fixing guide wires into a patient's bones. The secondary instrument 5 can be fixed to the distal housing 40 or the carriage 45 within the distal housing 40. The angular adjustments disclosed herein are primarily intended to adjust a relative position of the secondary instrument 5 relative to a patient's anatomy.

FIG. 4 illustrates a cross-sectional view of the adjustment assembly 10. The linkage block 65 pivots about the pin 62. The linkage block 65 houses a first linkage shaft 66 and generally positions the first linkage shaft 66 relative to the first angular adjustment shaft 64. The linkage shaft 66 is connected to the threading of the first angular adjustment shaft 64, such that the linkage shaft 66 essentially floats within the linkage block 65, and the linkage shaft 66 pushes the linkage block 65 in either direction when the first angular adjustment shaft 64 is rotated. In one aspect, the first linkage shaft 66 is constrained along two axes with respect to the linkage block 65. As the angular adjustment shaft 64 is rotated, the threaded region of the linkage shaft 66 moves along the axis of the threads of the angular adjustment shaft 64 thereby pushing the linkage block 65 along this axis and thereby causing the linkage block 65 to rotate about the pin 62.

As shown in FIG. 4, the linkage block 65 is fixed relative to the proximal housing 20. In one embodiment, the linkage block 65 can be formed integrally with the proximal housing 20. In another embodiment, the linkage block 65 can be fixed to the proximal housing 20 via other attachment configurations.

The first angular adjustment shaft 64 extends through openings 61a, 61b formed in the intermediate housing 60. The first linkage shaft 66 extends perpendicular to the first angular adjustment shaft 64.

Figure 6A:
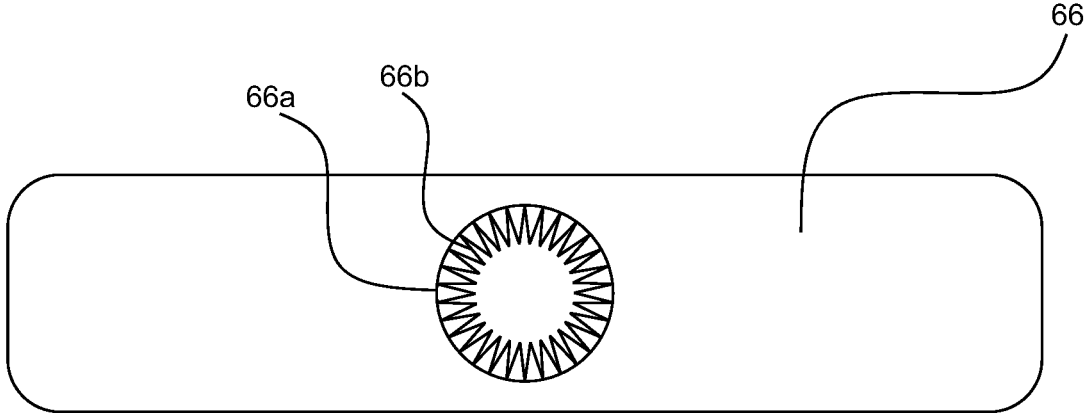
FIG. 6A illustrates features of a first linkage shaft.
Figure 6B:
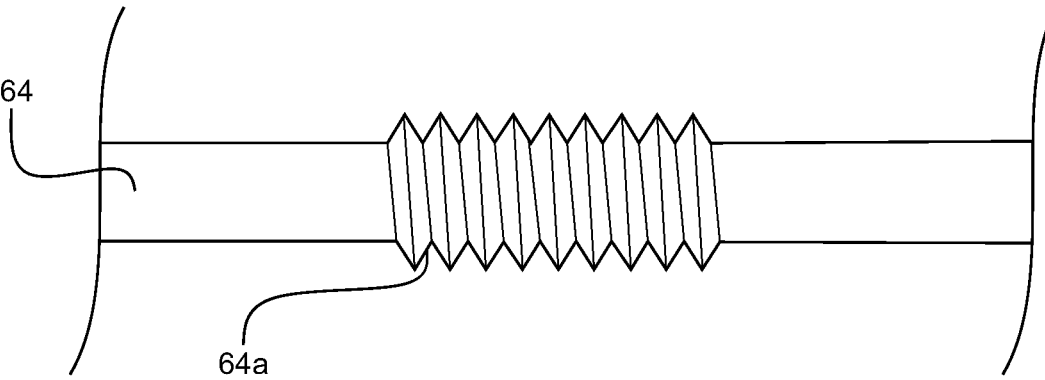
FIG. 6B illustrates features of a first angular adjustment shaft.

FIGS. 6A and 6B are simplified drawings to specifically only illustrate portions of the first linkage shaft 66 and the first angular adjustment shaft 64. As shown in FIG. 6A, in one embodiment the first linkage shaft 66 has a first threading 66b defined in a transversal opening 66a of the linkage shaft 66. For example, the first linkage shaft 66 can include a female threading that is oriented perpendicular relative to the longitudinal axis of the first linkage shaft 66. In another embodiment, the first linkage shaft 66 can include male threading or any other type of threading. The first angular adjustment shaft 64 extends perpendicular relative to the first linkage shaft 66 and inside the opening 66a of the first linkage shaft 66. As shown in FIG. 6B, the first angular adjustment shaft 64 includes a second threading 64a that is configured to mate with the first threading 66b on the first linkage shaft 66.

The first angular adjustment shaft 64 is configured to be rotated, and the first angular adjustment shaft 64 is fixed in a longitudinal or axial direction (i.e. the first angular adjustment shaft 64 is fixed in the left-right direction in FIG. 5 but is rotatable). To fix the first angular adjustment shaft 64, locking components 68a, 68b are provided. The locking components 68a, 68b can be formed integrally with the first angular adjustment shaft 64 or may be separately formed and then attached to the first angular adjustment shaft 64. As shown in FIG. 5, a first locking component 68a can be provided as an enlarged head of collar of the first angular adjustment shaft 64. A second locking component 68b can be provided as a washer that is fixed (e.g. welded) to an end of the first angular adjustment shaft 64.

In terms of operation, when the first angular adjustment shaft 64 is rotated, i.e. when a surgeon uses a tool to rotate a head or end formed on the first angular adjustment shaft 64, then the first angular adjustment shaft 64 rotates about its longitudinal axis in a linearly fixed orientation due to the locking components 68a, 68b. As a result of this rotation and the threadings 64a, 66b engaging with each other, the first linkage shaft 66, which is constrained to linear motion is driven along the first angular adjustment shaft 64. In one aspect, the first linkage shaft 66 is constrained by the position of its locking components 68a and 68b with respect to a length of the intermediate housing 60 through which the first linkage shaft 66 sits. In other words, the first linkage shaft 66 basically rides along the first angular adjustment shaft 64 as the first angular adjustment shaft 64 is rotated. The linear motion of the first linkage shaft 66 drives the linkage block 65 along the longitudinal axis of the first angular adjustment shaft 64.

Figures 3A, 3B:
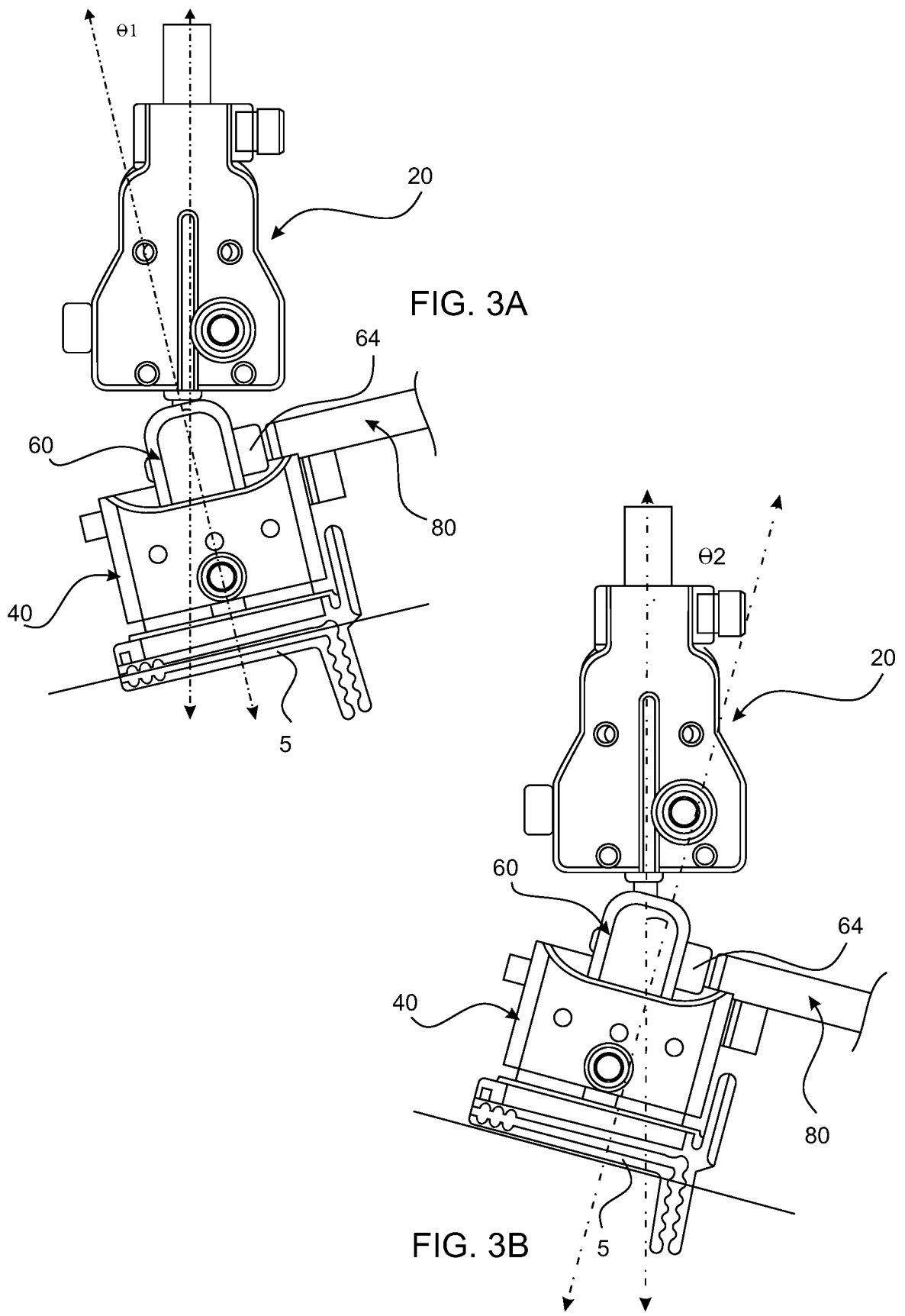
FIGS. 3A and 3B illustrate side views of the instrument during different states of adjustment using a first linkage.

Continuing with FIGS. 3A and 3B, various degrees of angular adjustment are illustrated. As shown in the figures, a tool 80 can be provided to manually engage the first angular adjustment shaft 64. The tool 80 can include any instrument, including handheld tools, e.g. a screwdriver, which is adapted to engage a surface of the first angular adjustment shaft 64 and impart rotational motion, i.e. twisting or turning motion, onto the first angular adjustment shaft 64. FIGS. 3A and 3B illustrate that the angle can be adjusted in two directions. The same tool 80 can be configured to engage both the first angular adjustment shaft 64 and the second angular adjustment shaft 44.

As shown in the drawings, the adjustment assembly 10 provides *varus*-valgus adjustment, i.e. adjustment in the coronal plane. For example, rotating the tool 80 clockwise can provide *varus* adjustment and rotating the tool 80 counter-clockwise can provide valgus adjustment, or vice versa. FIG. 3A shows an adjustment angle θ1, which can correspond to 15 degrees, and FIG. 3B shows an adjustment angle θ2, which can correspond to 15 degrees. The definition of *varus* and valgus is with respect to the patient's left or right extremity. As shown in FIG. 3A and FIG. 3B, the secondary instrument 5 is configured for a patient's right foot and therefore FIG. 3A shows a *varus* adjustment relative to the neutral position and FIG. 3B shows a valgus adjustment relative to the neutral position. Although the adjustment angles are not specifically annotated in FIGS. 3C-3E, the same range of adjustment can be provided using the other linkage and adjustment assembly.

Figure 3C:
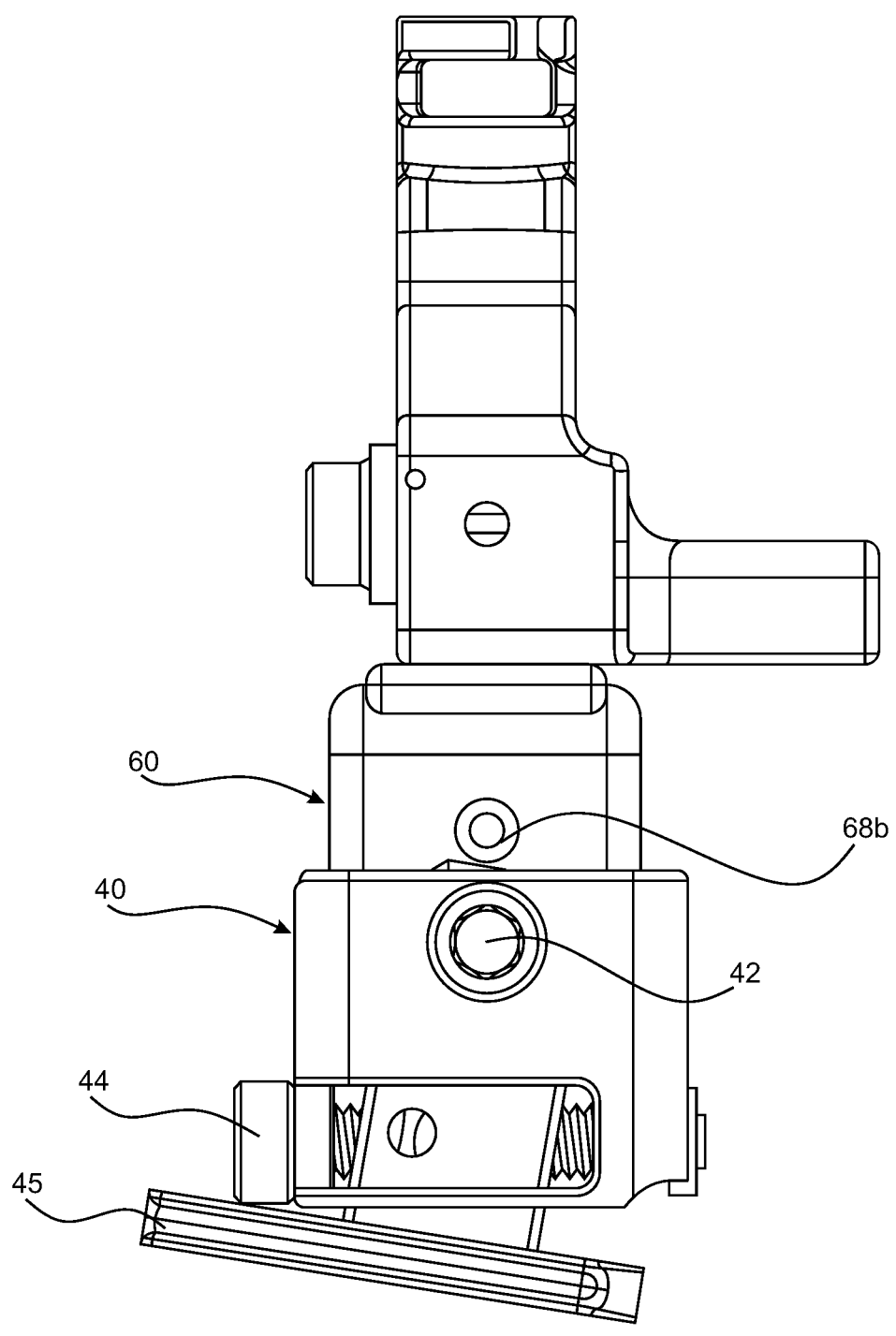
FIG. 3C is a side view of the instrument during adjustment in a first direction using a second linkage.
Figure 3D:
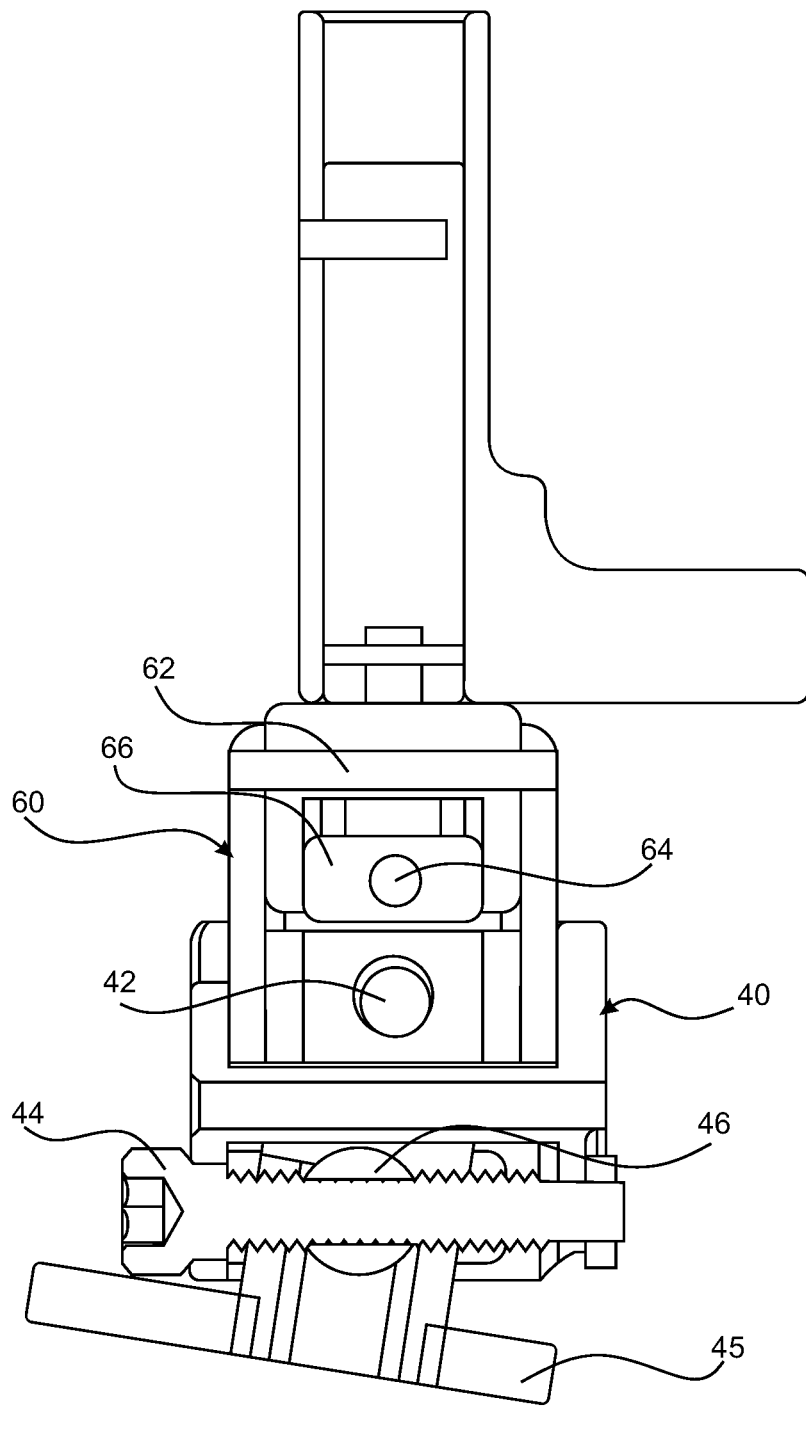
FIG. 3D is a side cross-sectional view of the instrument during adjustment in the first direction using the second linkage.

A second angular adjustment shaft 44 is provided, which functions according to the same mechanisms and features described above with respect to the first angular adjustment shaft 64. As shown in FIGS. 3D and 5, the carriage 45 is provided in the distal housing 40 (i.e. within the outer housing 40' of the distal housing 40), and the carriage 45 pivots about the shaft 42 when the second angular adjustment shaft 44 is actuated. A second linkage shaft 46 is constrained along two axes with respect to the carriage 45.

The second linkage shaft 46 can rotate about its long axis (which is perpendicular to its threaded axis) and move up and down with respect to the carriage 45. As the second angular adjustment shaft 44 is rotated, the threaded region of the second linkage shaft 46 moves along the axis of the threads of the second angular adjustment shaft 44 thereby pushing the carriage 45 along this axis and thereby causing the carriage 45 to rotate about the shaft 42.

Figure 3E:
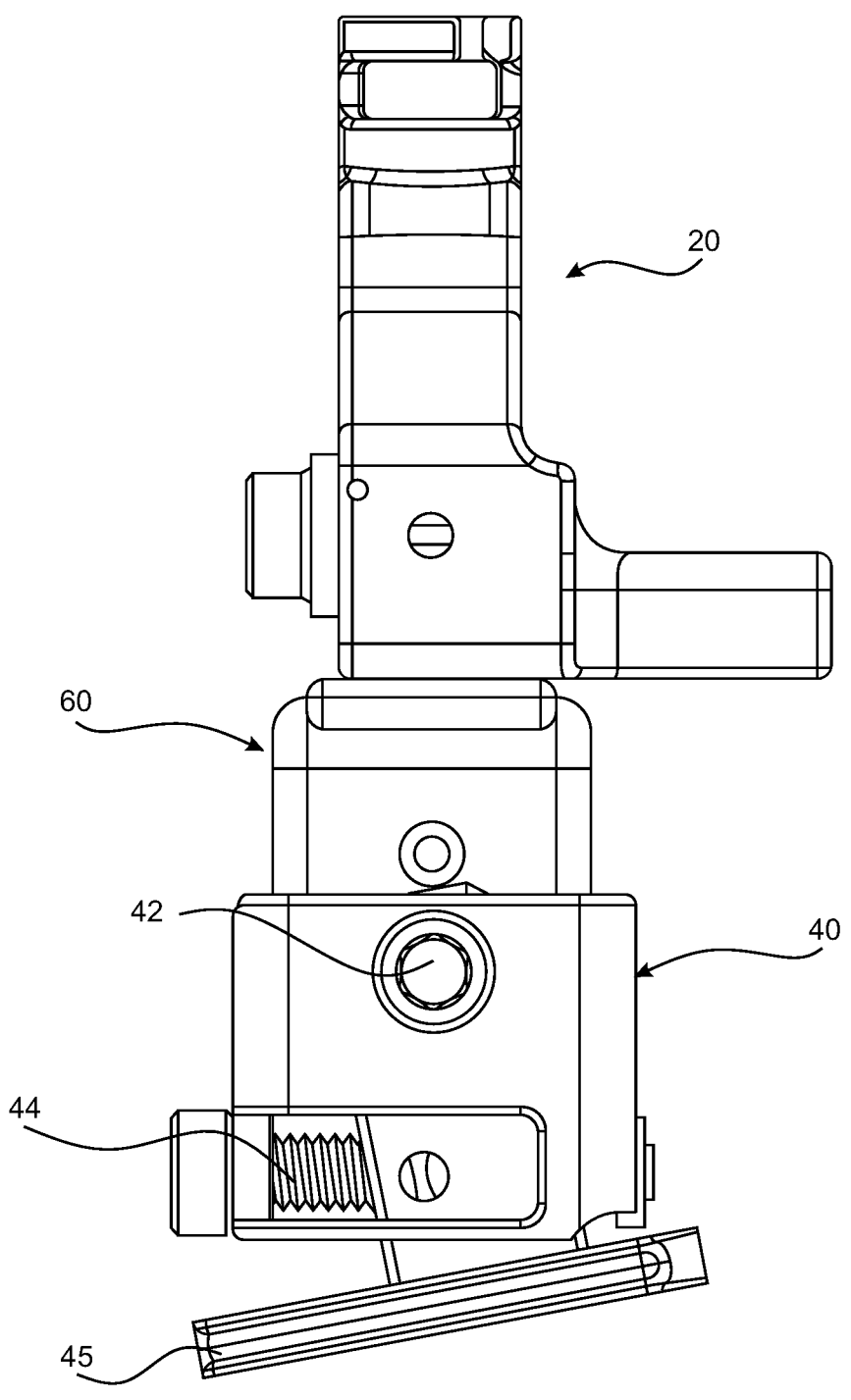
FIG. 3E is a side view of the instrument during adjustment in a second direction using the second linkage.

Actuation of the second angular adjustment shaft 44 generally converts rotational input applied to the second angular adjustment shaft 44 into linear motion imparted onto the second linkage shaft 46. The general function and operation of the second linkage B/angular adjustment shaft 44 is similar to the first linkage A/angular adjustment shaft 64. As shown in the drawings, there is threading on both the second angular adjustment shaft 44 and the second linkage shaft 46 to provide a driving engagement between the two components. The second linkage shaft 46 is housed within the carriage 45. The second linkage shaft 46 is driven linearly along a longitudinal axis of the second linkage shaft 46. The carriage 45 and the distal housing 40 are linked to each other about an axis of the shaft 42 but are otherwise mobile relative to each other and can be adjusted. Accordingly, any linear translation of motion between the second angular adjustment shaft 44 and the second linkage shaft 46 modifies a relative angular position between the carriage 45 and the distal housing 40. FIGS. 3C-3E illustrate various states of these adjustments. The threadings 44*a*, 46*b* on the second linkage shaft 46 and the second angular adjustment shaft 44 are not specifically described in more detail but are otherwise similar to the threadings 64*a*, 66*b*.

In one embodiment, the adjustments by the linkage systems A, B allow the surgeon to adjust the opening angle (commonly referred to as "slope") of the instrument relative to the patient's anatomy. In one embodiment, the adjustments by the linkage systems A, B allow the surgeon to adjust the *varus*-valgus angle of the instrument relative to the patient's anatomy. In one embodiment, both of the linkage systems A, B can utilize a screw type feature that actuates the instrument, causing it rotate about a fixed point, thereby adjusting the relative angle between the instrument and the bone. In one embodiment, these adjustments can be made between +45° and −45° from a line perpendicular to the long axis of the tibial instrument. In other words, linkage systems A, B allow a surgeon to precisely and accurately adjust a relative position of the secondary instrument 5 (i.e. a cutting guide or tool) relative to the patient. The linkage systems A, B permit adjustments and reduce the likelihood of misalignment and improves a surgeon's ability to precisely select the angle most appropriate for the patient.

Figure 9A:
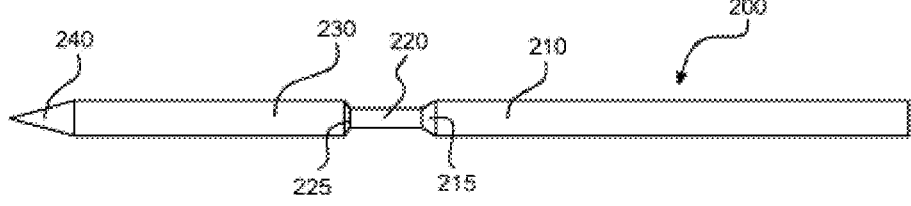
FIG. 9A is a side view of a guide wire according to one embodiment.
Figure 9B:
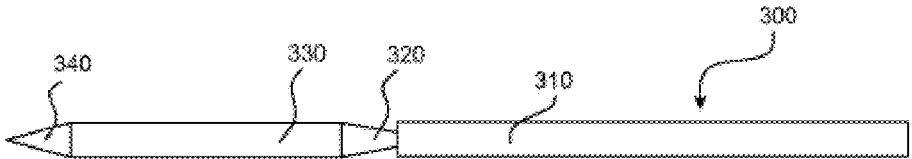
FIG. 9B is a side view of a guide wire according to another embodiment.

As shown in FIGS. 9A and 9B, a guide wire 200, 300 is provided that includes a varying profile. The modified profile of the guide wires 200, 300 provides for a more reliable sever point or breaking point due to the reduced thickness in the transition regions. This configuration helps reduce the cut or broken ends of the guide wires 200, 300 from interfering with any openings or holes on instruments as various instruments are placed onto the severed guide wires 200, 300. A depth or end point of the transition regions of the guide wires 200, 300 are selected such that the transition regions will remain outside of a patient's anatomy during a typical surgery. For example, the depth or end point of the transition regions is between 0.25 inches and 3.0 inches. In another embodiment, the transition regions are positioned at least ¼-⅓ of a total length of the guide wires 200, 300 away from the tips.

As shown in FIG. 9A, the guide wire 200 includes a proximal region 210, a transition region 220, a distal region 230, and a tip 240. As shown in FIG. 9A, the guide wire 200 has a generally cylindrical profile. A length of the guide wire 200 can vary on the particular size requirements dictated by the type of surgery and depth that is required for the guide wire 200. In a direction from the proximal region 210 to the transition region 220, a first connection portion 215 is provided. The first connection portion 215 has a tapered profile. A length of the transition region 220 is shorter than the proximal region 210 and the distal region 230. The transition region 220 is connected to the distal region 230 with a second connection portion 225. As shown in FIG. 9A, the second connection portion 225 has a shorter tapered profile than the profile of the first connection portion 215. The distal region 230 has a cylindrical profile, similar to the profile of the proximal region 210. A length of the distal region 230 is less than a length of the proximal region 210 in one embodiment. A thickness or diameter of the distal region 230 is different than a thickness or diameter of the transition region 220 in one embodiment. As shown in the drawings, the distal region 230 is thicker than the transition region 220. In one embodiment, a least a portion of an outermost diameter of the transition region 220 is less than 75% of a diameter of the distal region 230. The tip 240 is defined at an axial end of the distal region 230 opposite from the second connection portion 225. The tip 240 includes a point, that can have a tapered or trocar profile.

As shown in FIG. 9B, the guide wire 300 includes a proximal region 310, a transition region 320, a distal region 330, and a tip 340. The proximal region 310 is similar to the proximal region 210 and includes a generally cylindrical profile. The transition region 320 that tapers from a larger end (connected to the distal region 330) to a smaller end (connected to the proximal region 310). The distal region 330 has a generally cylindrical profile, similar to the distal region 230. The distal region 330 terminates with the tip 340. A taper of the transition region 320 is similar to the taper of the tip 340 but in an opposite direction or orientation. In one embodiment, a taper of the tip 340 is greater than a taper of the transition region 320.

The guide wires 200, 300 can be used in the adjustment assembly 10 disclosed herein and can be inserted into the guide wire openings on various parts of the adjustment assembly 10.

Figure 10A:
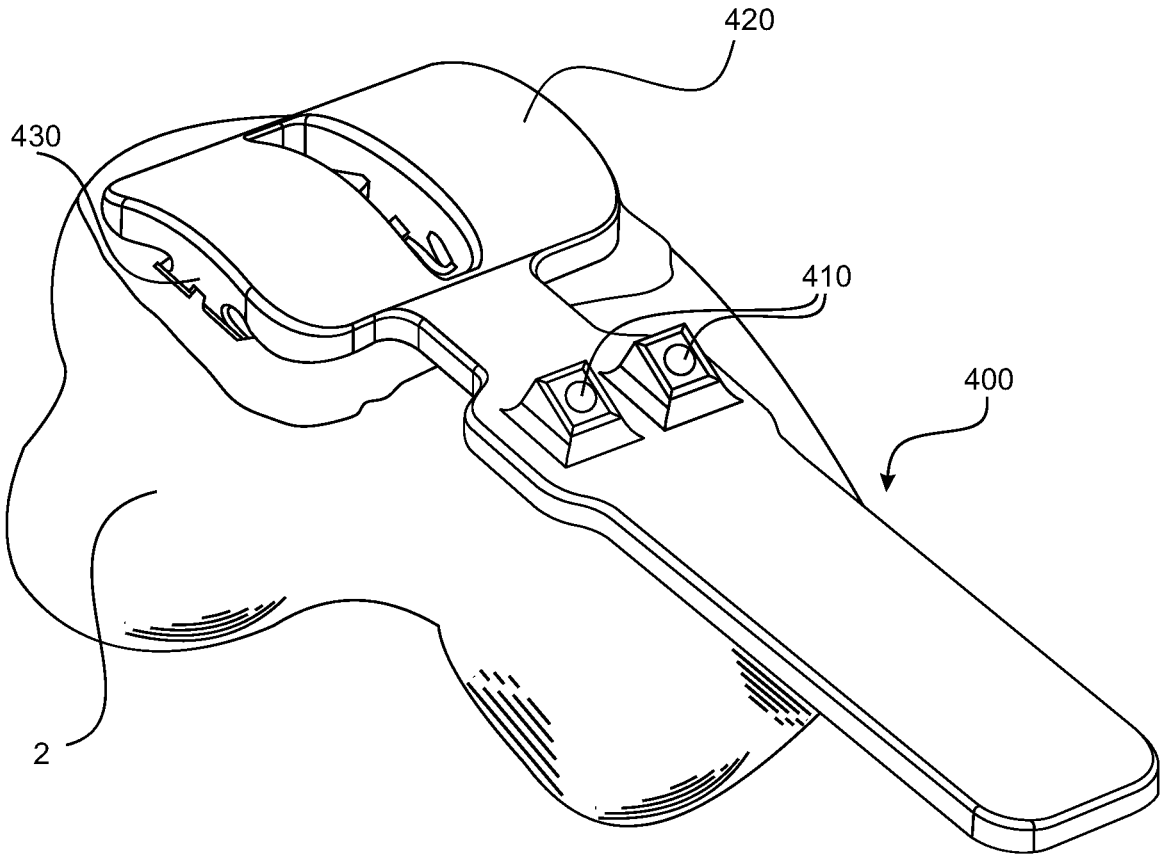
FIGS. 10A-10D illustrate various steps of using the guide wires of either FIG. 9A or 9B.

In use, a surgeon would align a first surgical instrument 400 onto a patient's talus 2 (as shown in FIG. 10A) and insert at least one guide wire 200 into a guide hole 410 in the first surgical instrument 400. Once the guide wire 200 is inserted into a patient's anatomy, at least a portion of the transition region 220 is configured to remain outside of a patient's bone, i.e. talus 2. Regarding the first instrument 400, this instrument 400 can include the guide holes 410, a sizing surface 420 shaped to approximate a size of an implant, and other profile features 430 that are shaped to approximate other features on the implant.

Figure 10B:
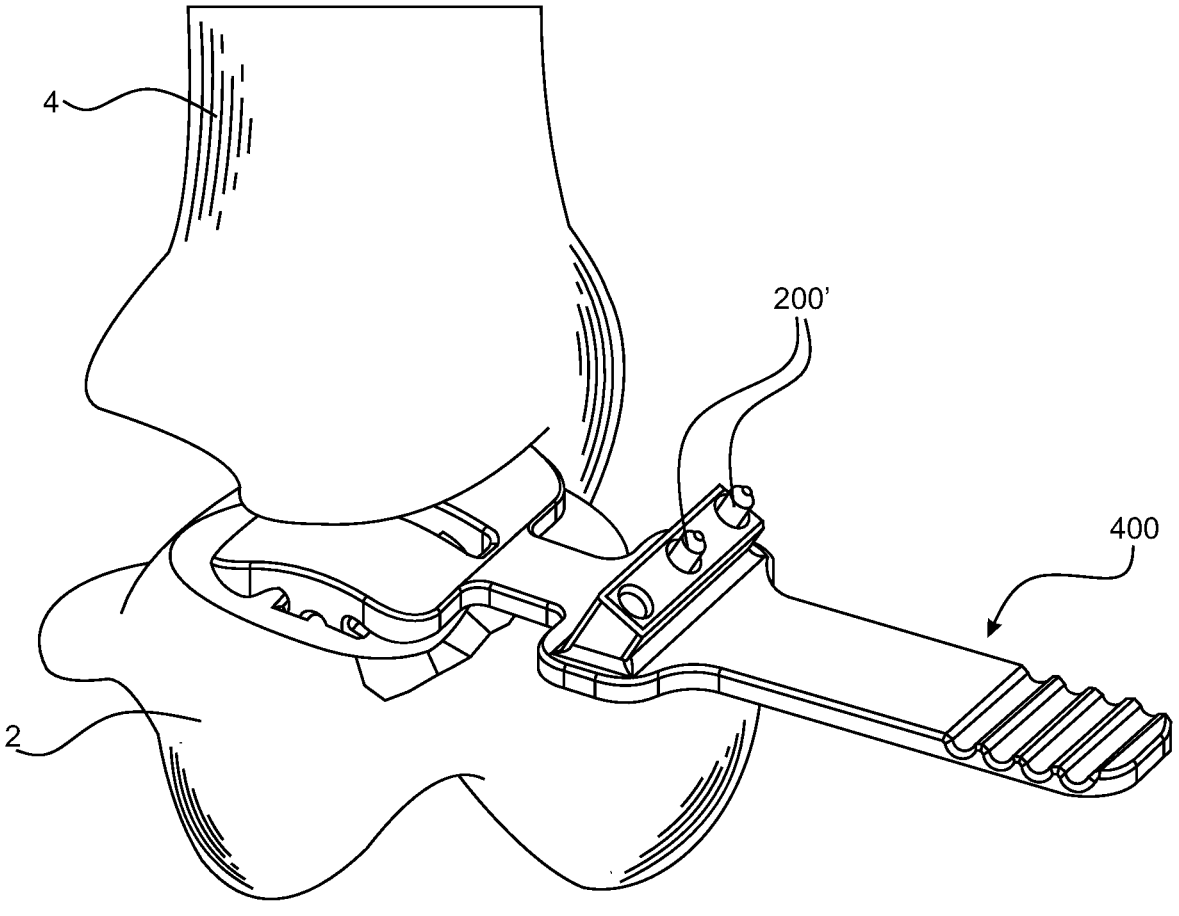
Figure 10C:
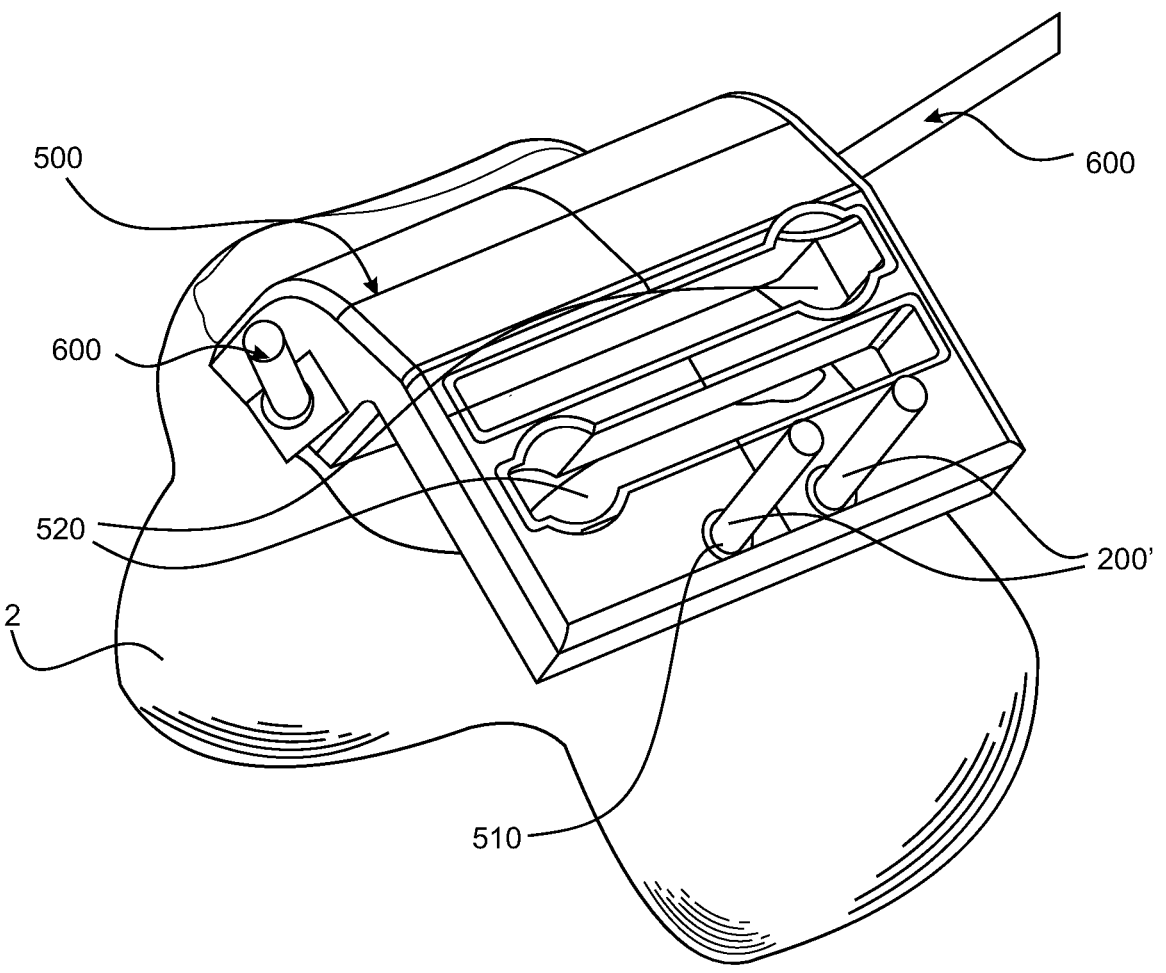
Figure 10D:
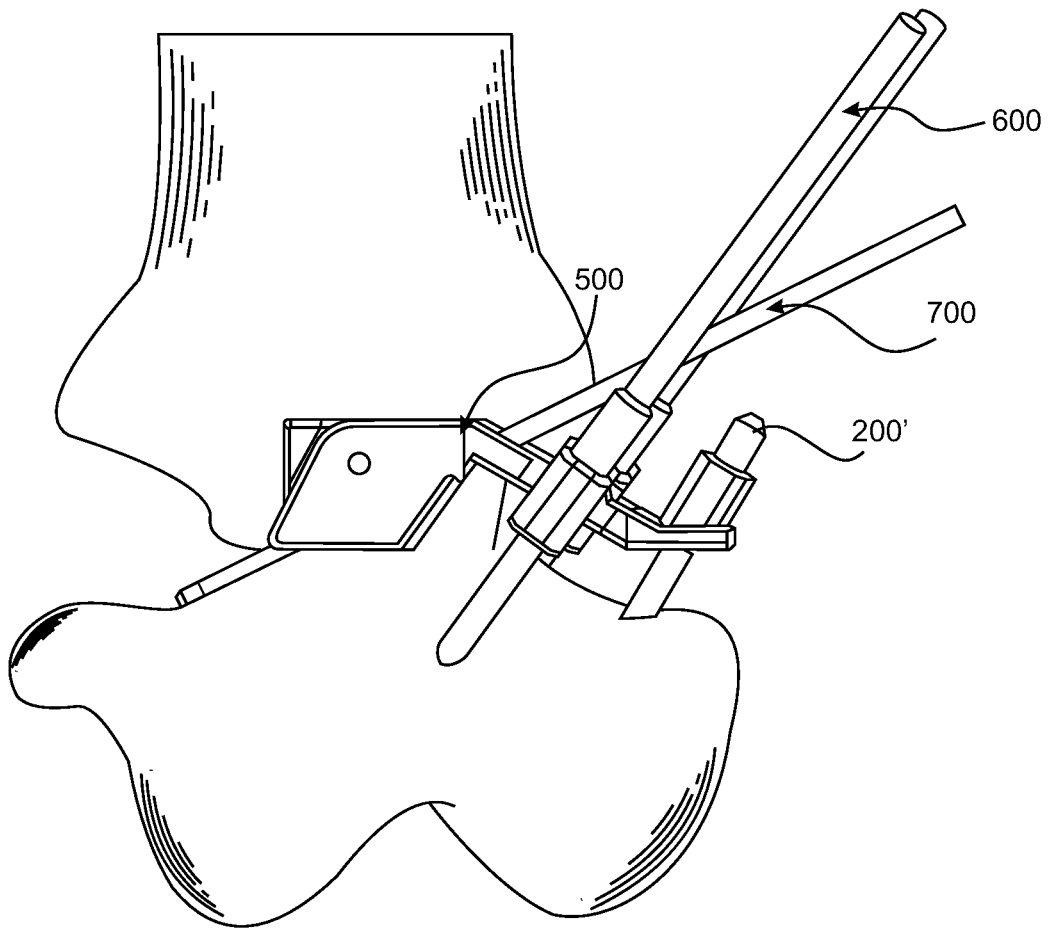

The surgeon cuts or severs the guide wire 200 in the transition region 220, as shown in FIG. 10B. After removing the first surgical instrument 400, the surgeon then positions a second surgical instrument 500 with respect to a remaining portion of the now severed guide wire 200′, as shown in FIG. 10C. The second surgical instrument 500 includes guide holes 510 for the severed guide wires 200′ and at least one opening, aperture, slot, or hole 520 dimensioned or configured to receive or accept a cutting device 700 (shown in FIG. 10D). The cutting device 700 is generally configured to remove a portion of a patient's talus 2.

An additional element 600 can be provided to further stabilize the second instrument 500. The additional element 600 can include a tool, guide wire, instrument, bone screw, or other type of element capable of fixing a position of the second surgical instrument 500.

In another embodiment, the method of using the guide wire 200 can include inserting the guide wire 200 into a guide hole 410 of a first instrument 400, removing the first instrument 400, positioning a second instrument 500 with respect to the guide wire 200, and then severing the guide wire 200 in the transition region 220. In other words, the sequence of removing the instruments and cutting or severing the guide wire 200 can vary.

Features of the first and second instruments 400, 500 can vary. The guide wire 200 has a profile that prevents the guide wire 200 from having a splayed or deformed severed end such that the guide holes 410, 510 of the instruments 400, 500 are incapable of sliding over the severed guide wires 200'.

One of ordinary skill in the art would understand from this disclosure that any one or more of the embodiments can be used in connection with any one or more of the steps described herein.

Having thus described the present invention in detail, it is to be appreciated and will be apparent to those skilled in the art that many physical changes, only a few of which are exemplified in the detailed description of the invention, could be made without altering the inventive concepts and principles embodied therein.

It is also to be appreciated that numerous embodiments incorporating only part of the preferred embodiment are possible which do not alter, with respect to those parts, the inventive concepts and principles embodied therein.

The present embodiment and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

The invention claimed is:

1. A method of using a surgical guide wire comprising: a distal tip having a tapered or trocar end configured for insertion into a bone;

a distal region adjacent to the distal tip, the distal region configured to be partially inserted into the bone;

a transition region adjacent to the distal region, the transition region including a portion with a smaller diameter than a diameter of the distal region; and a proximal region adjacent to the transition region, wherein the transition region provides a reliable sever point or breaking point for the surgical guide wire, the method comprising:

aligning a first surgical instrument relative to a patient anatomy;

inserting the guide wire through the first surgical instrument and into the patient anatomy such that at least a portion of the transition region remains outside of the patient anatomy;

severing or breaking the guide wire at the sever or breaking point, such that a portion of the guide wire remains in the patient anatomy;

removing the first surgical instrument from the patient anatomy; and positioning a second surgical instrument with respect to the guide wire.

2. The method of claim 1, wherein at least a portion of the transition region has a diameter that is less than 75% of a diameter of the distal region.

3. The method of claim 1, wherein the transition region is positioned at least ¼-⅓ of a total length of the guide wire away from the distal tip.

4. The method of claim 1, wherein the transition region has a tapered profile, with a larger end connected to the distal region and a smaller end connected to the proximal region.

5. The method of claim 4, wherein the tapered profile is in an opposite orientation to a profile of the distal tip.

6. The method of claim 4, wherein the tapered profile is different to a profile of the distal tip.

7. The method of claim 1, wherein the transition region has a uniform profile having a smaller diameter than the proximal region or the distal region, and a first connection portion between the transition region and the proximal region has a first tapered profile, and a second connection portion from the transition region to the distal region has a second tapered profile.

8. The method of claim 7, wherein the first tapered profile is different than the second tapered profile.

* * * * *